(12) United States Patent
Truckai

(10) Patent No.: US 11,517,342 B2
(45) Date of Patent: Dec. 6, 2022

(54) SURGICAL CUTTING DEVICE WITH GEAR MECHANISM

(71) Applicant: Meditrina, Inc., San Jose, CA (US)

(72) Inventor: Tamas J. Truckai, Saratoga, CA (US)

(73) Assignee: Meditrina, Inc., San Jose, CA (US)

( * ) Notice: Subject to any disclaimer, the term of this patent is extended or adjusted under 35 U.S.C. 154(b) by 422 days.

(21) Appl. No.: 16/678,647

(22) Filed: Nov. 8, 2019

(65) Prior Publication Data

US 2020/0146703 A1 May 14, 2020

Related U.S. Application Data

(60) Provisional application No. 62/758,389, filed on Nov. 9, 2018.

(51) Int. Cl.
| | | |
|---|---|---|
| *A61B 17/16* | (2006.01) | |
| *A61B 17/32* | (2006.01) | |
| *A61B 17/3205* | (2006.01) | |
| *A61B 17/3207* | (2006.01) | |
| *A61B 1/045* | (2006.01) | |
| *A61B 1/015* | (2006.01) | |

(52) U.S. Cl.
CPC ........ *A61B 17/32002* (2013.01); *A61B 1/015* (2013.01); *A61B 1/045* (2013.01); *A61B 17/320758* (2013.01); *A61B 2017/320032* (2013.01)

(58) Field of Classification Search
CPC .............. A61B 17/32002; A61B 1/045; A61B 17/320758; A61B 2017/320032; A61B 2017/0046; A61B 2017/320028; A61B 17/320068; A61B 1/00066; A61B 1/0052; A61B 17/3205; A61B 17/00; A61B 1/00; A61B 2565/00; A61B 17/00234; A61B 2017/00367; A61B 2017/00535; A61B 17/14; A61B 17/32; A61B 17/16

See application file for complete search history.

(56) References Cited

U.S. PATENT DOCUMENTS

| | | | |
|---|---|---|---|
| 5,054,149 A | 10/1991 | Si-Hoe et al. | |
| 5,529,494 A | 6/1996 | Vlacancich | |
| 5,618,293 A | 4/1997 | Sample et al. | |
| 5,954,654 A * | 9/1999 | Eaton | A61M 25/0136 600/459 |
| 6,520,971 B1 * | 2/2003 | Perry | A61B 17/2909 606/139 |
| 8,142,463 B2 | 3/2012 | Arcenio et al. | |
| 8,882,680 B2 | 11/2014 | Furlong et al. | |
| 10,342,572 B2 | 7/2019 | Govari et al. | |
| 2003/0163126 A1 | 8/2003 | West | |
| 2004/0147934 A1 | 7/2004 | Kiester | |
| 2005/0125009 A1 * | 6/2005 | Perry | A61B 17/2909 606/139 |
| 2011/0184233 A1 * | 7/2011 | Fructus | A61B 1/018 600/104 |

(Continued)

FOREIGN PATENT DOCUMENTS

WO WO 2020/097445 5/2020

*Primary Examiner* — Shaun L David
*Assistant Examiner* — Mitchell Brian Hoag
(74) *Attorney, Agent, or Firm* — Levine Bagade Han LLP

(57) ABSTRACT

An integrated hysteroscopic treatment system which includes an endoscopic viewing system, a fluid management system, a resecting device and a controller for operating all the systems.

15 Claims, 24 Drawing Sheets

(56) References Cited

U.S. PATENT DOCUMENTS

| | | | |
|---|---|---|---|
| 2012/0004595 A1* | 1/2012 | Dubois | A61B 17/32002 |
| | | | 606/49 |
| 2014/0100558 A1* | 4/2014 | Schmitz | A61B 17/285 |
| | | | 606/174 |
| 2014/0336643 A1* | 11/2014 | Orczy-Timko | A61B 18/149 |
| | | | 606/45 |
| 2016/0235469 A1 | 8/2016 | Prisco et al. | |
| 2017/0049952 A1 | 2/2017 | Jezierski et al. | |
| 2017/0078583 A1* | 3/2017 | Haggerty | A61B 1/00071 |
| 2017/0175852 A1* | 6/2017 | Nicholas | F16H 1/22 |
| 2018/0028212 A1* | 2/2018 | Akilian | A61B 17/320783 |
| 2018/0042641 A1 | 2/2018 | Govari et al. | |
| 2018/0140307 A1* | 5/2018 | Bono | A61B 17/1626 |
| 2019/0008541 A1* | 1/2019 | Norton | A61B 17/1626 |
| 2019/0183528 A1* | 6/2019 | Sullivan | A61B 17/320016 |

* cited by examiner

SURGICAL CUTTING DEVICE WITH GEAR MECHANISM

RELATED APPLICATION

This application claims benefit of U.S. provisional application 62/758,389 filed on Nov. 9, 2018, the entirety of which is incorporated by reference. This application is also related to PCT application PCT/US2019/060445 filed Nov. 8, 2019, the entirety of which is incorporated by reference herein.

BACKGROUND OF THE INVENTION

The present invention relates to an integrated hysteroscopic treatment system, which includes an endoscopic viewing system, a fluid management system, a resecting device and a controller for operating all the systems.

SUMMARY OF THE INVENTION

The present disclosure includes tissue resection systems for resecting tissue in a fluid-filled working space. For example, such a system can include a working end comprising inner and outer sleeves having respective inner and outer cutting windows, wherein the inner sleeve is adapted to rotate to provide window-open and window-closed positions; a controller operatively connected to a negative pressure source in communication with a flow channel having first cross-sectional area in the inner sleeve; an aperture arrangement in the surface of either the inner or outer sleeve opposing a respective inner or outer cutting window; and a control algorithm adapted to maintain a selected set pressure in the working space between 10 mmHg and 200 mmHg during at any angle of rotation of the inner sleeve relative to the outer sleeve.

In another variation, the system can include a control algorithm that is adapted to maintain said selected set pressure when the inner sleeve is stopped relative to the outer sleeve in any rotational position. For example, the control algorithm can comprise a PID control algorithm.

In another variation, the tissue resection system comprises an inner window, outer window and aperture arrangement that define a combined open area for accommodating fluid outflows in response to the negative pressure source, and wherein said combined open area varies at each degree of 360° rotation of the inner sleeve relative to the outer sleeve, and wherein the minimum combined open area varies from the maximum combined open area during said 360° of rotation by a factor that does not impinge on continuous function the PID control algorithm to maintain said selected set pressure.

In yet another variation, the tissue resection system includes an inner window, outer window and aperture arrangement define a combined open area for accommodating fluid outflows in response to the negative pressure source, and wherein said combined open area varies at each degree of 360° rotation of the inner sleeve relative to the outer sleeve, and wherein the minimum combined open area varies from the maximum combined open area during said 360° of rotation by a factor that does not impinge on continuous function the PID control algorithm to maintain said selected set pressure.

In an additional variation, the minimum combined open area varies from the maximum combined open area during said 360° of rotation by less than 50%. The open area can also vary by less than 40%, less than 30% or less than 20%.

Another variation of a tissue resection device for resecting tissue in a fluid-filled working space, comprises a device working end comprising inner and outer sleeves having respective inner and outer cutting windows, wherein the inner sleeve is adapted to rotate between window-open and window-closed positions; an aperture arrangement in the surface of either the inner or outer sleeve opposing a respective inner or outer cutting window; a controller operatively coupled to a negative pressure source connected to a flow channel in the inner sleeve for providing a fluid outflows from the fluid-filled working space through a combination of the inner window, outer window and aperture arrangement at any selected rotational position of the inner sleeve relative to the outer sleeve; and wherein the controller utilizes a PID control algorithm for maintaining a set pressure in the fluid-filled working space, and where at any selected set pressure, the flow rate of said fluid outflows at any window-open or window-closed position varies less than 50%.

In another variation, a tissue resection device includes a device working end comprising inner and outer sleeves having respective inner and outer cutting windows, wherein the inner sleeve has an interior flow channel and is adapted to rotate between window-open and window-closed positions; an aperture arrangement in the surface of the inner or outer sleeve opposing a respective inner or outer cutting window; wherein the flow channel has a first cross-sectional area and the combination of the inner window, outer window and aperture arrangement at a selected rotational position of the inner sleeve relative defines a minimum second cross-sectional area; and wherein the ratio of said second cross-sectional area to said first cross-sectional area is at least 0.5:1.

Variations of the tissue resection device include a ratio of the second cross-sectional area to the first cross-sectional area to be at least 0.6:1, at least 0.7:1 or at least 0.8:1.

In an additional variation, a tissue resecting device includes a handle carrying a motor having a drive shaft coupled to a gear mechanism having an output shaft; a tubular cutter comprising inner and outer sleeves having respective inner and outer cutting windows, where the inner sleeve is adapted to rotate between window-open and window-closed positions; and wherein the inner sleeve is coupled to the output shaft, and the gear mechanism is configured to covert one-directional rotation of the drive shaft to oscillating rotation of the output shaft and inner sleeve.

A variation of such a system can include a gear mechanism that converts 360° rotation of the drive shaft into oscillation of the output shaft comprising at 360° rotation of the output shaft in a clockwise direction and at least 360° rotation of the output shaft in a counter-clockwise direction.

The present disclosure also includes an endoscopic viewing system. For example, such an endoscopic viewing system can include an endoscope configured for single use comprising a handle coupled to an elongated shaft carrying an image sensor; and control actuators carried in the handle including at least an actuator for image capture, an actuator for controlling fluid flows from a fluid management system, and an actuator for controlling set pressure.

The descriptions provided herein are examples of the invention described herein. It is contemplated that combinations of specific embodiments, specific aspects or combinations of the specific embodiments themselves are within the scope of this disclosure.

BRIEF DESCRIPTION OF THE DRAWINGS

Additional aspects of the invention will become clear from the following description of illustrative embodiments and from the attached drawings, in which.

DETAILED DESCRIPTION OF THE INVENTION

Figure 1A:
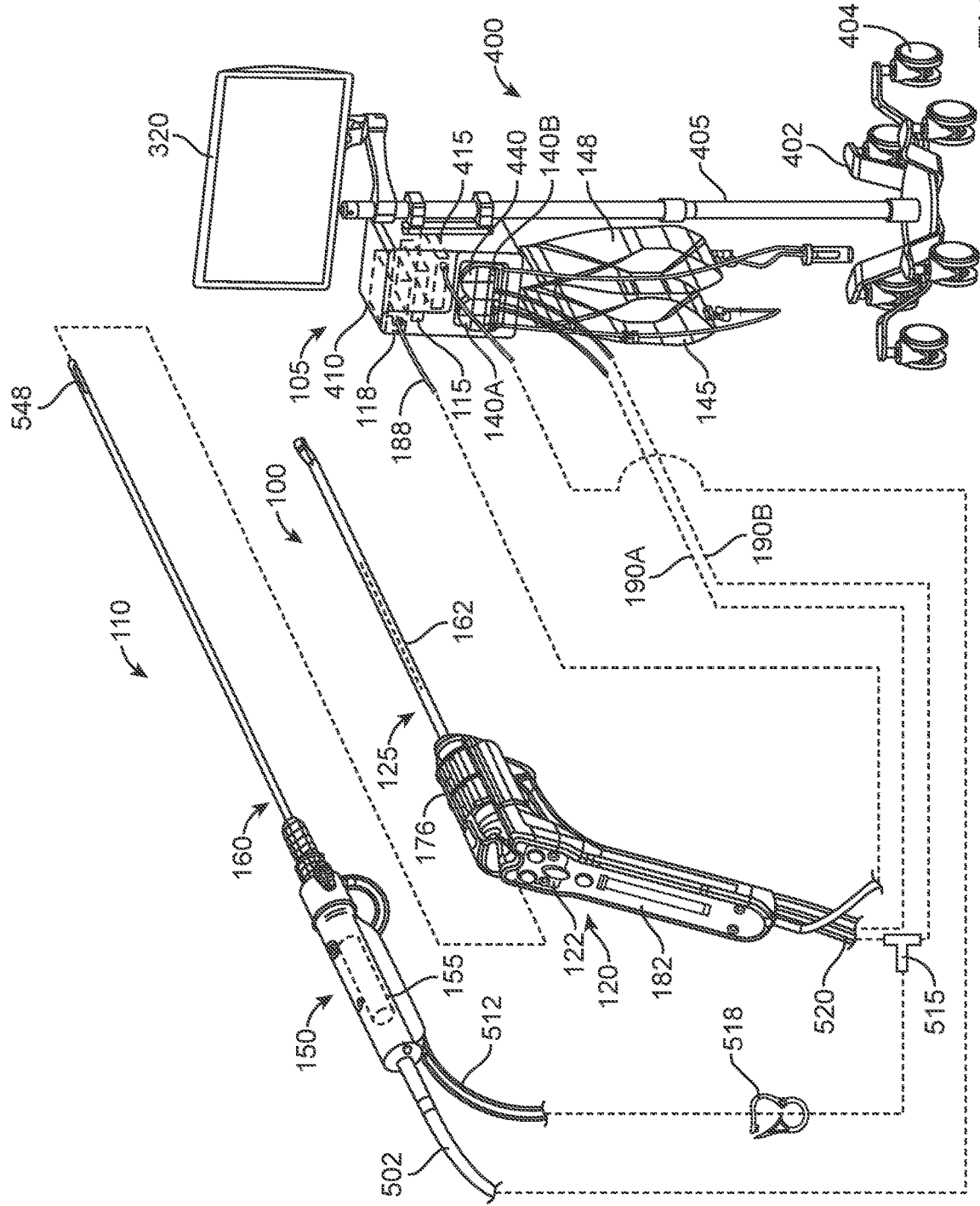
FIG. 1A is a perspective view of components of a hysteroscopic treatment system corresponding to the invention, including an endoscopic viewing system, a fluid management system and a resecting device.

FIG. 1A illustrates a hysteroscopic treatment system 50 corresponding to the invention, which comprises multiple components including an endoscopic viewing system 100, a fluid management system 105 and a resection device 110 that are all operated by a controller 115 in a base unit 118 with integrated software algorithms configured to operate all the systems and subsystems.

More in particular, the endoscopic viewing system 100 of FIGS. 1A, 1B, 2A and 2B includes a re-usable handle component 120 with a finger-actuated control pad 122 and a disposable endoscope component 125 that carries a distal electronic imaging sensor 128. The fluid management system 105 includes a first peristaltic inflow pump 140A and second peristaltic outflow pump 140B, a fluid source 145 and fluid collection reservoir 148 together with a fluid weight measurement subsystem. The resection device 110 includes a re-usable handpiece 150 with a motor drive 155 and a disposable cutting component 160 for resecting tissue in a hysteroscopic procedure, for example, used for resecting uterine polyps. Each of the systems and subsystems will be described in more detail below.

Endoscopic Viewing System

Figure 1B:
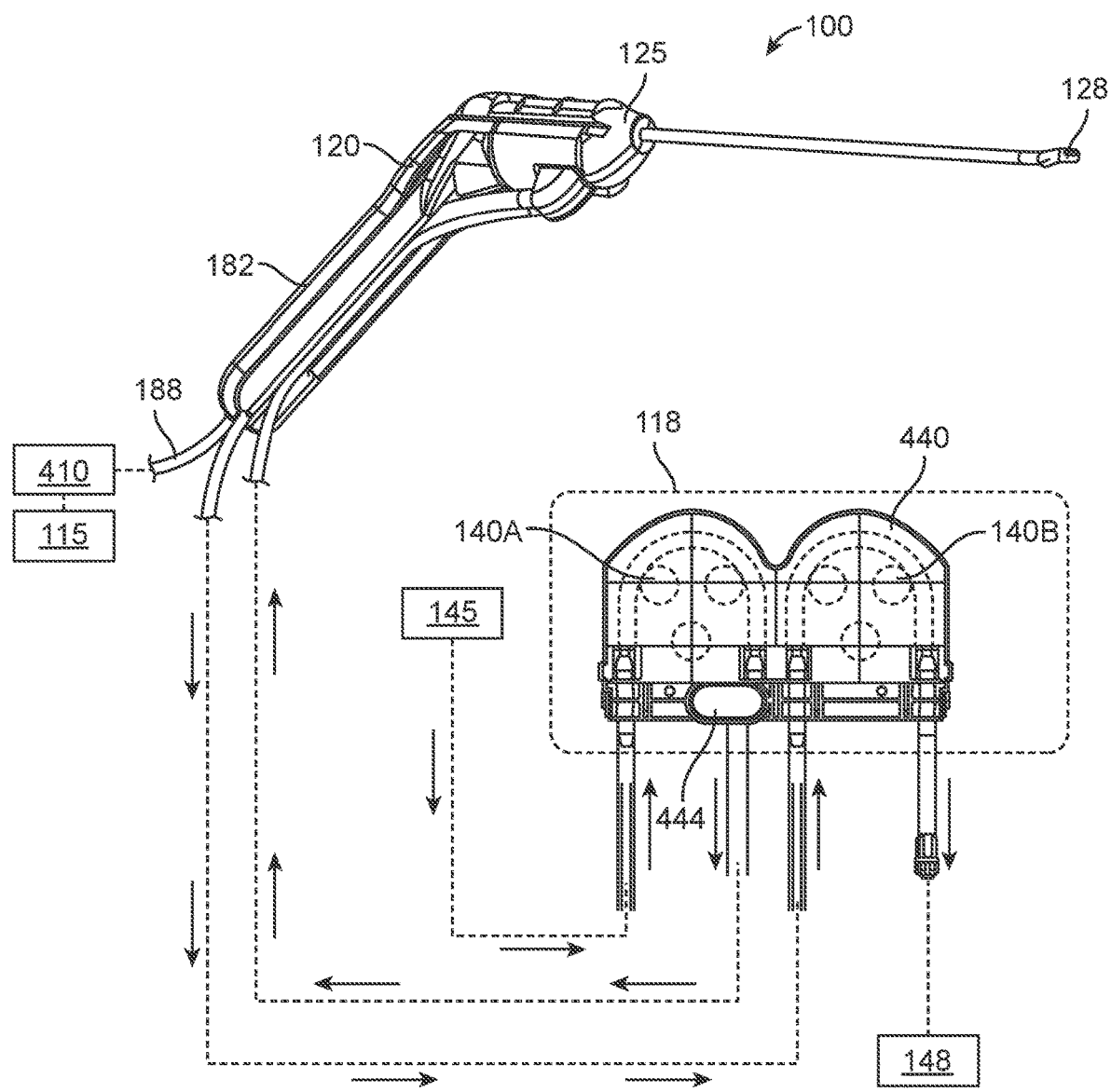
FIG. 1B is a perspective view of the endoscopic viewing system and a schematic view of the fluid management system of FIG. 1A.
Figure 2A:
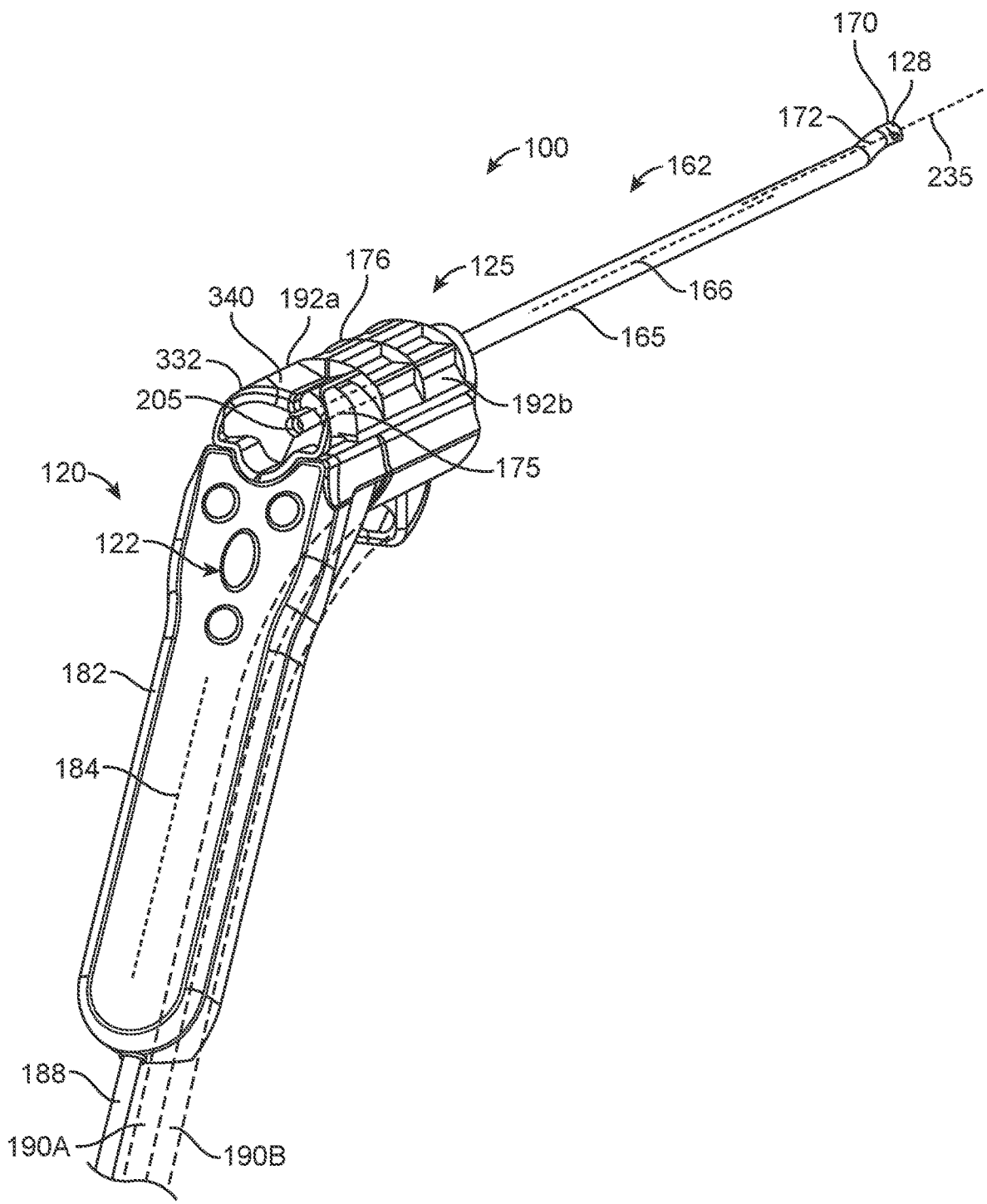
FIG. 2A is a perspective view of the endoscopic viewing system of FIG. 1B from a different angle.
Figure 2B:
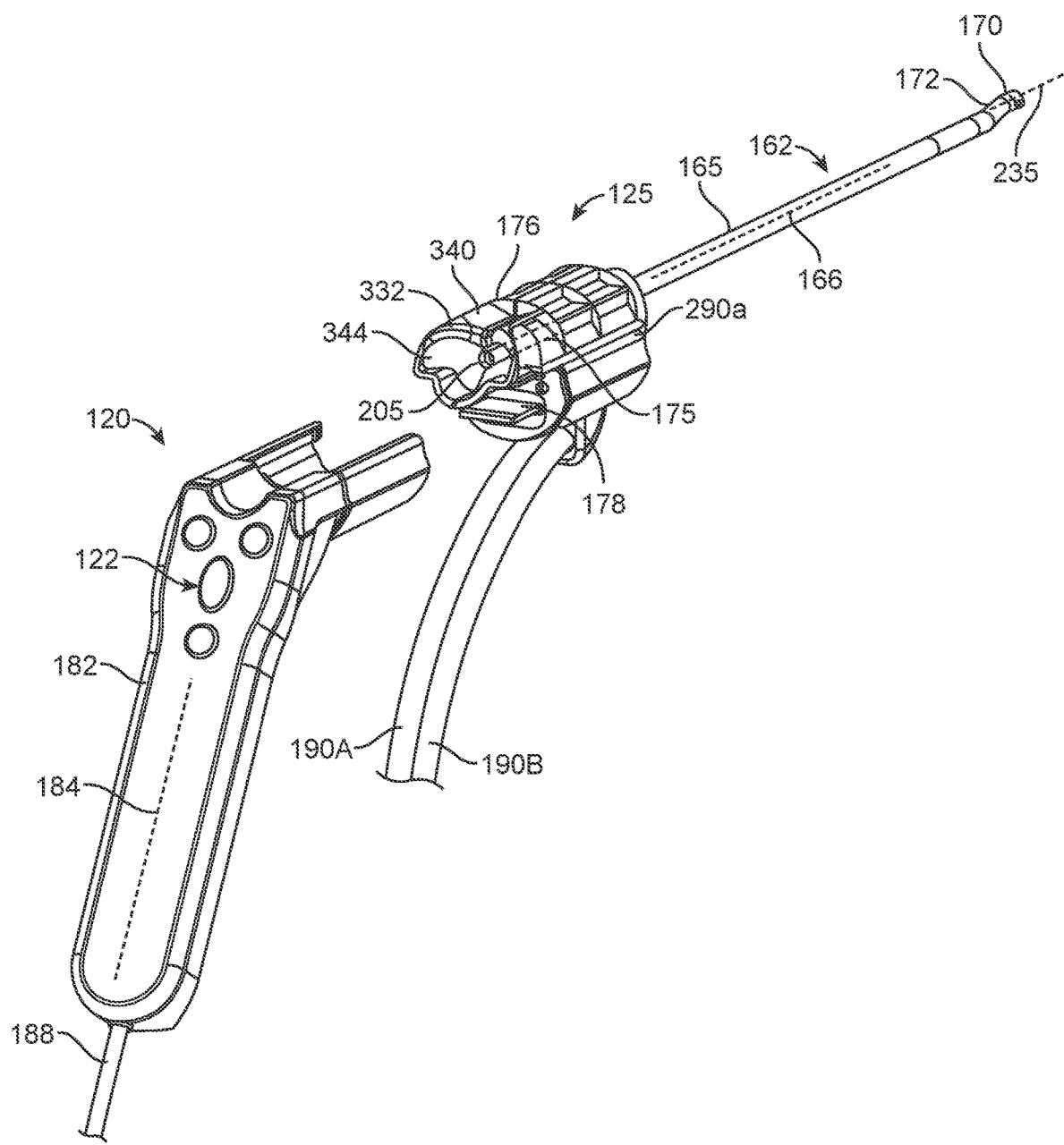
FIG. 2B is a perspective view of the endoscopic viewing system of FIG. 2A showing a single-use disposable endoscope component separated from a re-usable handle component.

Referring to FIGS. 1B, 2A and 2B, it can be seen that the endoscopic viewing system 100 includes a handle component 120 and a detachable single-use endoscope component 125. The endoscope shaft assembly 162 has a straight proximal portion 165 that extends about a central longitudinal axis 166. The shaft includes a distal tip section 170 that is offset from the longitudinal axis 166. A shaft transition section 172 extends at an angle between the straight proximal shaft portion 165 and the offset distal tip section 170. The imaging sensor 128 is disposed at the distal end of the offset tip section 170. As can be seen in FIGS. 2A-2B, the endoscope component 125 has a working channel 175 extending therethrough, which will be described in more detail below. In one variation, endoscope shaft assembly 162 has a diameter ranging between 4 mm and 10 mm with an overall length configured for use in hysteroscopy. More commonly, the shaft diameter is from 5 mm to 6 mm in diameter.

In one variation, the endoscope component 125 has a hub 176 that is adapted for sliding, detachable engagement with the handle component 120 as can be best seen in FIG. 2B. The endoscope shaft assembly 162 extends distally from the hub 176 and the angled transition section 172 and distal tip section 170 are oriented in a superior or upward direction relative to the hub 176. As can be seen in FIG. 2B, the hub 176 carries a projecting electrical connector 178 that is adapted to couple to a mating electrical connector 180 in the handle component 120 that can be best seen in FIG. 3. In some variations, the endoscope shaft assembly 162 may be rotated relative to the hub 176 (not shown in FIGS. 2A-2B). While FIGS. 2A-2B illustrates that the endoscope component 125 is configured for axial sliding engagement with the handle component 120, it should be appreciated that the angled pistol grip portion 182 of the handle component 120 could plug into the endoscope component 125 in a different arrangement, such as a male-female threaded connector aligned with the axis 184 of the angled grip portion 182. As will be described below, the endoscope component 125 comprises a sterile device for use in the sterile field, while the handle component 120 may not be sterilized and is typically adapted for use in a non-sterile field. A cable 188 extends from the handle to an imaging processor 410, controller 115 and power source described further below (FIGS. 1A-1B).

Figure 9A:
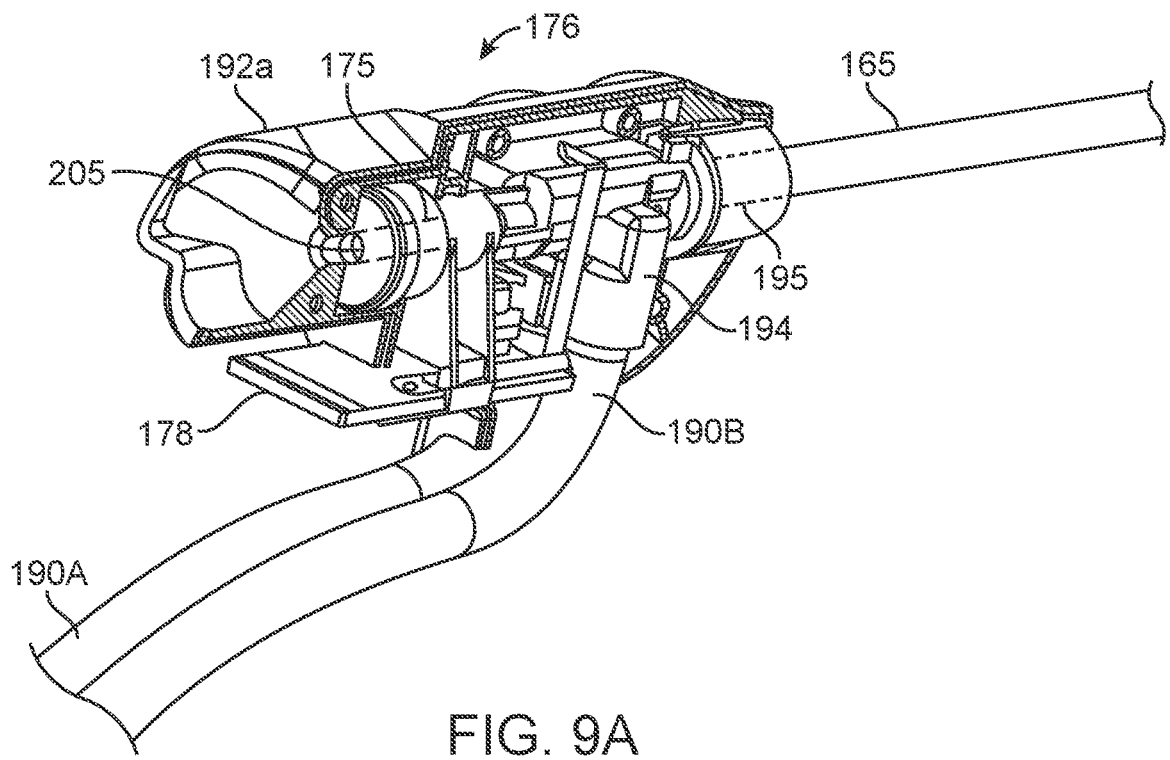
FIG. 9A is another perspective view of a partially disassembled endoscope component of the system of FIGS. 1A-2B showing inflow and outflow channels in a channel housing and a flex circuit coupled to the image sensor and the pressure sensor.
Figure 9B:
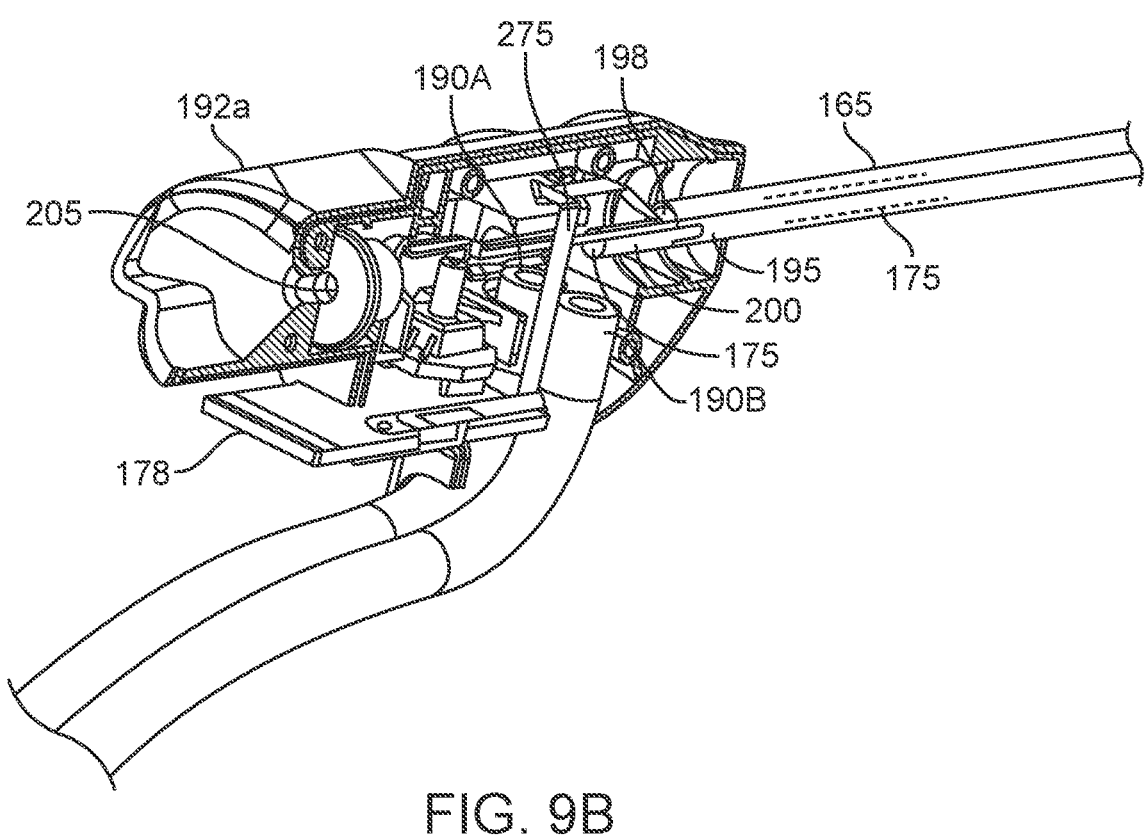
FIG. 9B is a perspective view similar to that of FIG. 9A with the channel housing removed to show the inflow and outflow channels in the shaft assembly.

As can be seen in FIGS. 1A, 1B and 2B, the endoscope component 125 includes fluid inflow tubing 190A and fluid outflow tubing 190B that communicate with the fluid management system 105, which is further described below and shown generally in FIGS. 1A-1B. As can be understood from FIGS. 2B and 9A, the endoscope hub 176 can consist of two injection molded plastic shell elements 192a and 192b, and FIG. 9A shows one side element removed to the interior of the hub 176. It can be seen that both the inflow tubing 190A and outflow tubing 190B are coupled to an injection-molded flow channel housing 194 in the hub 176 that is fixed to the proximal end 195 of the endoscope shaft assembly 162. FIG. 9B is a cut-away view similar to that of FIG. 9A with the housing 194 removed to show that inflow tubing 190A communicates with an open space or flow channel 198 extending through the endoscope shaft assembly 162 that is outward from the thin-wall sleeve 200 that defines the working channel 175 therein. The flow channel 198 can also be seen in FIGS. 6A-6B at its distal termination 202 in the endoscope shaft assembly 162. As can be understood from FIG. 9B, the outflow tubing 190B communicates with a proximal end 204 of sleeve 200 and working channel 175, which also can be seen in FIGS. 6A-6B. In a method of use that will be described below, the endoscope shaft assembly 162 can be navigated through a patient's endocervical canal with the inflow and outflow pumps 140A and 140B (see FIGS. 1A-1B) operating to provide continuous irrigation to the distal tip of the endoscope component 125 together with endoscopic viewing by means of the image sensor 128. Such a variation will thus allow fluid inflows through channel 198 and fluid outflows through the working channel 175.

Now turning to FIGS. 6A-6B, the endoscope shaft assembly 162 has a small insertion profile or configuration that consists of the outer diameter of the shaft assembly, which includes the proximal straight section 165, the angled section 172 that is relatively short as will be described further below and the distal section 170 (see FIG. 6A). Of particular interest, referring to FIG. 6B, the distal portion of the endoscope shaft assembly 162 includes a working channel portion 175' that is re-configurable between a first smaller cross-section as shown in FIG. 6A for accommodating fluid outflows and a second larger cross-section as shown in FIG. 6B for accommodating a shaft of the resecting device 110 (FIG. 1A) or another similar tool shaft.

Figure 6A:
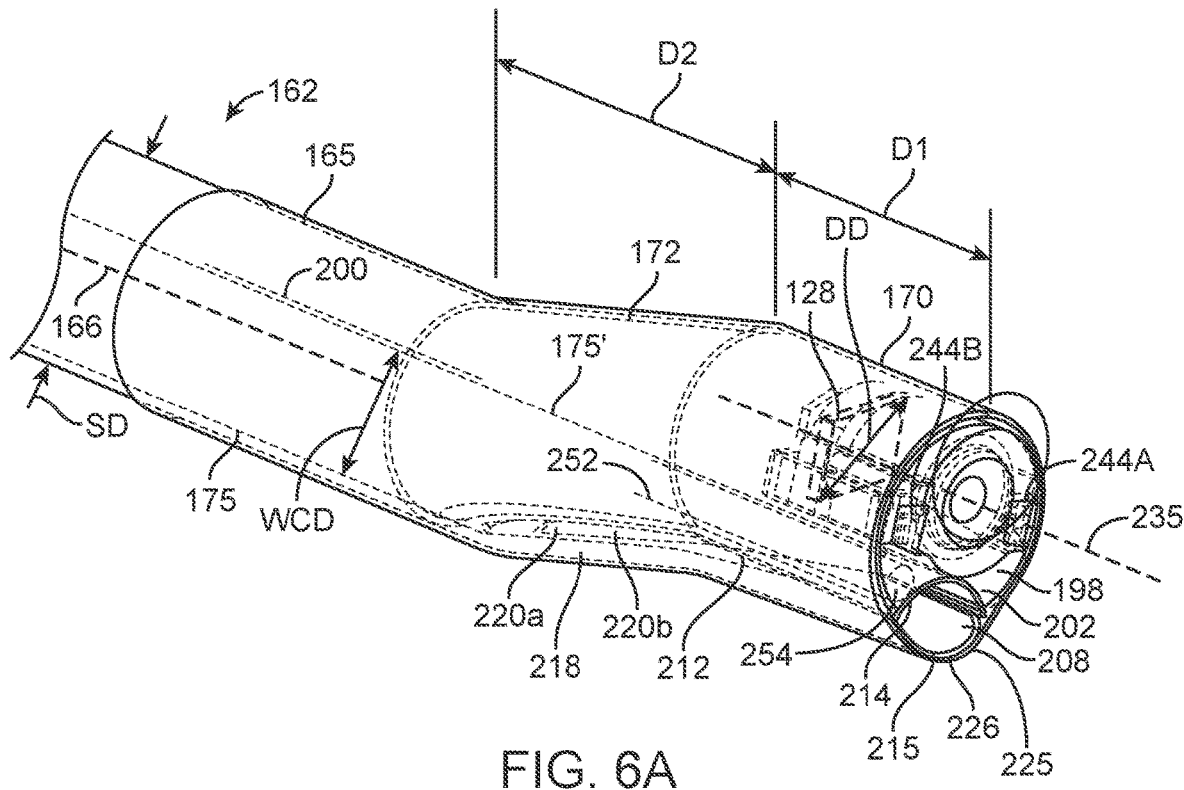
FIG. 6A is an enlarged perspective view of the distal end of the endoscope shaft assembly showing a working channel with a distal channel portion in a reduced cross-sectional configuration for introduction into a patient's body.
Figure 6B:
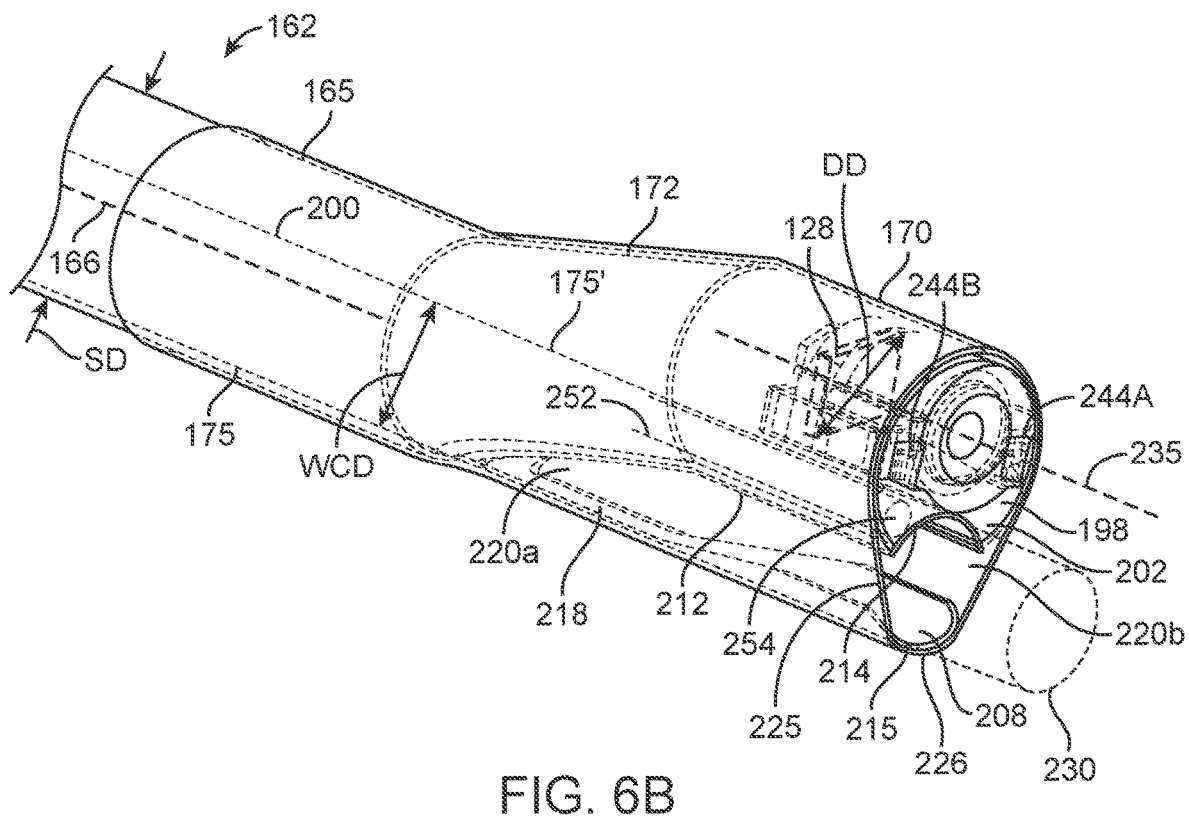
FIG. 6B is another view of the distal end of the endoscope shaft assembly of FIG. 6A showing the distal working channel portion in an expanded cross-sectional configuration when a tool shaft is introduced through the working channel.

In one variation shown in FIGS. 2B and 6B, it can be seen that the sleeve 200 that defines the working channel 175 extends in a straight configuration through the endoscope component 125 from its proximal end 205 to its open distal termination 208. As can be seen in FIGS. 6A and 6B, the distal end 212 of sleeve 200 has a superior surface 214 that is straight and rigid. The working channel sleeve 200 has an inferior or lower sleeve portion 215 that is flexible and in one variation has a living hinge portion 218 below sidewall cut-outs 220a and 220b in the sleeve 200. Further, the distal end of the endoscope component 125 includes an elastomeric sleeve 225 that surrounds the angled shaft portion 172 and the distal shaft section 170 as well as a distal portion of the proximal straight shaft 165. Thus, as can be seen in FIG. 6A, the elastomeric sleeve 225 has sufficient elastic strength to collapse or constrict the working channel portion 175' to the smaller cross-section as seen in FIG. 6A.

As can be seen in FIG. 6A, the lower sleeve portion 215 includes a sleeve wall 226 with sufficient curvature to maintain an open pathway through the working channel 175 when the elastomeric sleeve 225 constricts the working channel portion 175', which thereby always provides an open fluid outflow pathway. For example, the sleeve wall 226 can have the diameter as a proximal portion of sleeve 200 and extend over a radial angle ranging from 30° to 90°. While the lower sleeve portion 215 shown in FIG. 6A comprises a portion of the wall of metal sleeve 200, in another variation, the flexible lower sleeve portion 215 may be any bendable plastic material or a combination of plastic and metal.

FIG. 6B next shows the working channel portion 175' in its second expanded configuration as when a physician inserts an elongated tool shaft 230 (phantom view) through the working channel 175. Such a tool shaft 230 will initially slide along the hinge portion 218 of the lower sleeve portion 215 and then stretch the elastomeric sleeve 225 to open distal working channel portion 175' to allow the tool shaft 230 to extend through the working channel. In other words, the elastomeric sleeve 225 will be stretched or deformed to a tensioned position as shown in FIG. 6B as a tool shaft 230 is inserted through the distal working channel portion 175'. When the tool shaft 230 is withdrawn from the working channel portion 175', the elastomeric sleeve 225 will return from the tensioned position of FIG. 6B to the repose or non-tensioned position of FIG. 6A to return the working channel portion 175' to the constricted configuration FIG. 6A.

In general, the endoscope component 125 corresponding to the invention allows for the use of an image sensor 128 having a large diagonal dimension relative to the insertion profile or diameter of the endoscope shaft assembly 162 while at the same time providing a working channel 175 that has a large working channel diameter WCD relative to the insertion profile or diameter of the endoscope shaft assembly 162. More in particular, the endoscope component 125 comprises a shaft assembly 162 having a shaft diameter SD extending to a distal shaft section 170, an image sensor 128 with a diagonal dimension DD carried by the distal shaft section 170 and a working channel 175 having a diameter WCD extending through the shaft assembly 162, wherein the working channel portion 175' in the distal end of the shaft assembly 162 is adjustable in shape to accommodate a tool shaft introduced therethrough and wherein the combination or the sensor's diagonal dimension DD and the working channel diameter WCD is greater than the shaft diameter SD (see FIG. 6B). In a variation, the sensor diagonal dimension DD is greater than 50% of the shaft diameter SD or greater than 60% of the shaft diameter. In a variation, the working channel diameter WCD is greater than 30% of the shaft diameter, greater than 40% of the shaft diameter or greater than 50% of the shaft diameter. In other words, the working channel portion 175' in the distal end is adjustable between a first cross-sectional dimension and a second cross-section dimension. In the variation of FIGS. 6A-6B, the working channel portion 175' in the distal region of the endoscope shaft assembly 162 is adjustable between an a partially constricted shape and a non-constricted shape.

In one variation, referring to FIG. 6A, the distal section 170 of the endoscope shaft assembly 162 has an axial dimension D1 ranging from 5 mm to 20 mm. Also referring to FIG. 6A, the angled shaft section 172 extends over a similar axial dimension D2 ranging from 5 mm to 20 mm. Still referring to FIG. 6A, the central axis 235 of distal shaft section 170 can be parallel to and offset from the longitudinal axis 166 of the straight shaft section 165 by a distance ranging from 1 mm to 8 mm.

Figure 7:
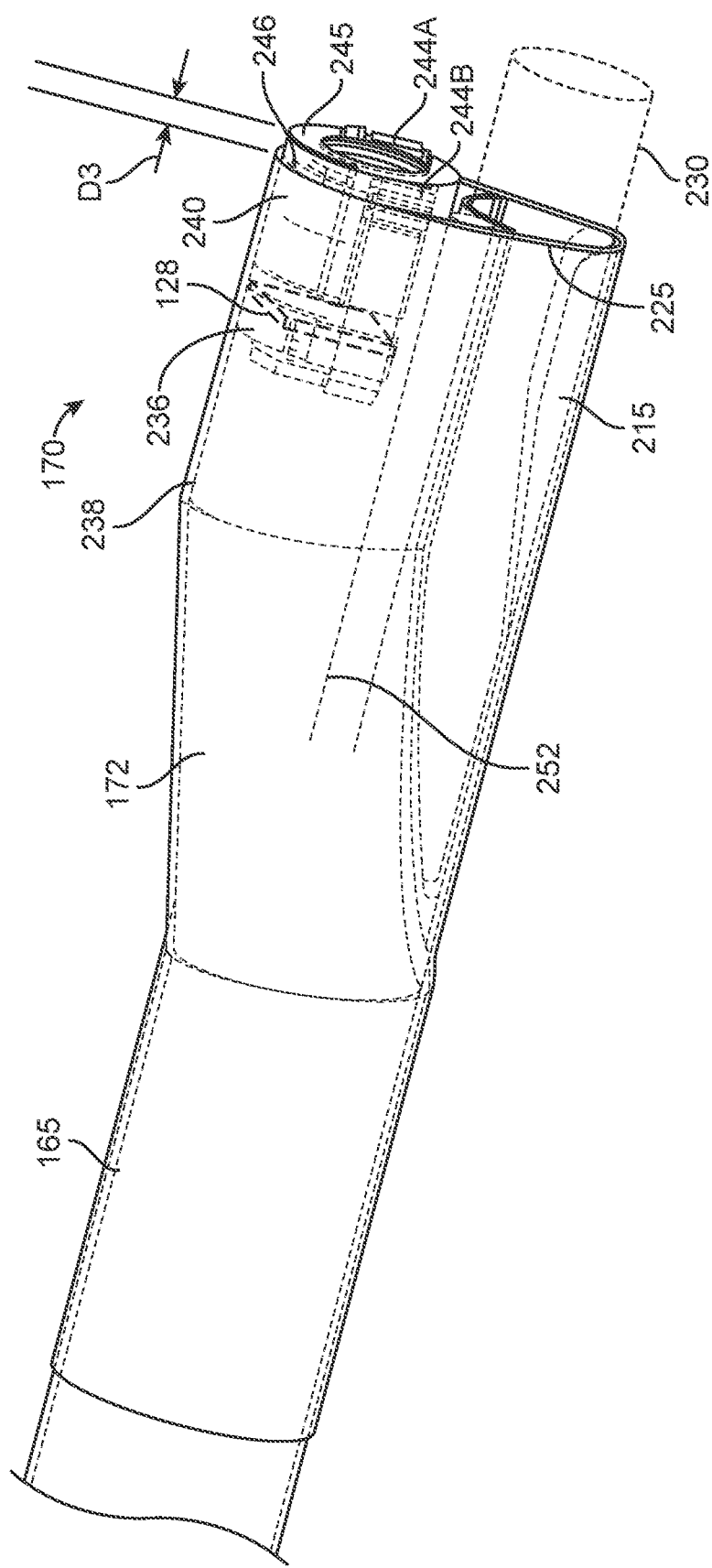
FIG. 7 is another view of the distal end of the endoscope shaft assembly of FIG. 6B showing an image of the distal working channel portion in an expanded cross-sectional sensor and lens stack.

Now turning to FIG. 7, the image sensor 128 is carried in a housing 236 that also carries a lens assembly 240 as is known in the art. The sensor and lens housing 236 is then carried in a thin wall sleeve 238 that comprises the distal endoscope section 170. Further, one or more light emitters, for example, LEDs indicated 244A and 244B carried on either side of the image sensor housing 236. Of particular interest, the distalmost surface 245 of the lens assembly 240 and the LEDs 244A and 244B is disposed distally outward from the distal end 246 of the thin-wall sleeve 238 as shown in FIG. 7. It has been found that providing such a distalmost surface 245 of the lens assembly and the LEDs outwardly from the shaft sleeve 238 improves lighting from the LEDs 244A and 244B as well as improving the field of view of the image sensor 128. The distance indicated at D3 in FIG. 7 can range from 0.2 mm to 2.0 mm.

Figure 8:
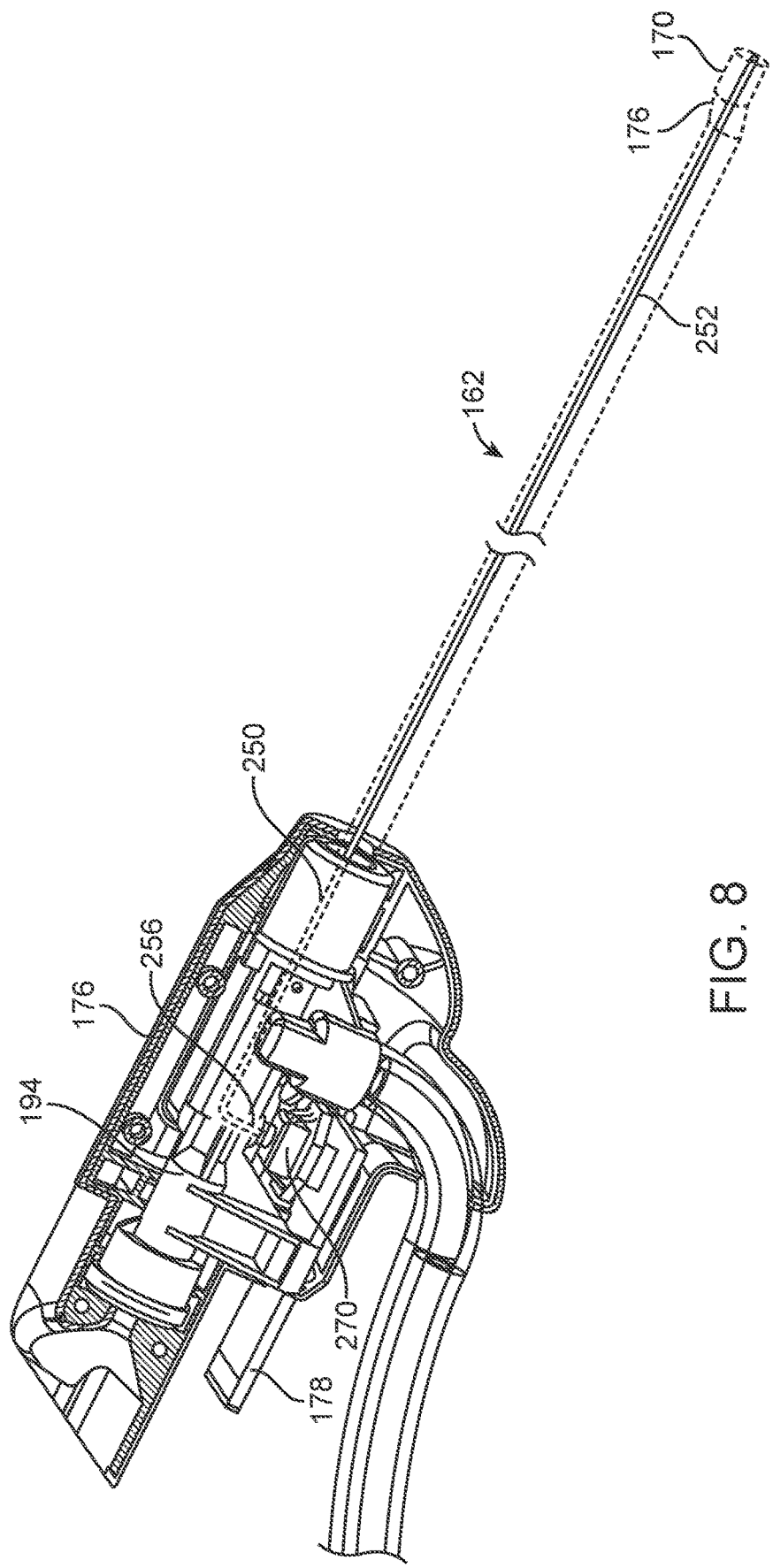
FIG. 8 is a perspective view of a partially disassembled endoscope component of the system of FIGS. 1A-2B showing a dedicated pressure sensing channel and disposable pressure sensor.

Now referring to FIGS. 7 and 8, another aspect of the invention comprises a dedicated fluid pressure sensing channel 250 that extends through a thin wall sleeve 252 in the endoscope shaft assembly 162. As can be seen in FIGS. 6A-6B, the distal end 254 of the pressure sensing sleeve 252 is open in the distal surface of the endoscope component 125. Referring to FIG. 8, the proximal end 256 of the pressure sensing channel 250 extends to the housing 194 in the hub 176 to communicate with a disposable pressure sensor 270. The pressure sensor 270 has electrical leads coupled thereto through the electrical connector 178 in hub 176 to thereby send electrical signals indicating pressure to the controller 115 (FIG. 1A) as will be described further below. Thus, in one aspect, the disposable endoscope component carries a single-use pressure sensor 270 coupled by a detachable connector to a remote controller 115.

In one variation, referring to FIG. 8, the thin wall sleeve 252 consists of a hydrophobic material, which can be any suitable polymer such as PFTE, having an interior diameter ranging from 0.25 mm to 2.5 mm. Often, the inner diameter of the thin wall sleeve 252 is between 0.5 mm and 1.5 mm. It has been found that a hydrophobic surface in the pressure sensing channel 250 will prevent the migration of fluid into the channel and thereby trap an air column in the channel communicating with the pressure sensor 270. The compressibility of the air column in the pressure sensing channel 250 is not significantly affected by the sensed pressure since the channel diameter is very small. In another variation, the metal sleeve 252 can be coated with a hydrophobic surface or an ultrahydrophobic surface.

Now turning to FIGS. 6A and 9B, the image sensor 128 and LEDs 244A and 244B are connected to an elongated flex circuit 275 that extends from electrical connector 178 in hub 176 through the endoscope shaft assembly 162. It has been found that only a flex circuit 275 is capable of carrying a sufficient number of electrical leads to the image sensor 128, the LEDs and the pressure sensor 270 to provide for system operation, wherein the number of electrical leads can range from 10 to 100. Further, the flex circuit 275 can extend through the shaft assembly 162 with an interior space that also functions as the fluid flow channel since the flex circuit 275 adequately insulates all the electrical leads.

Handle Component of the Endoscopic Viewing System

Figure 3:
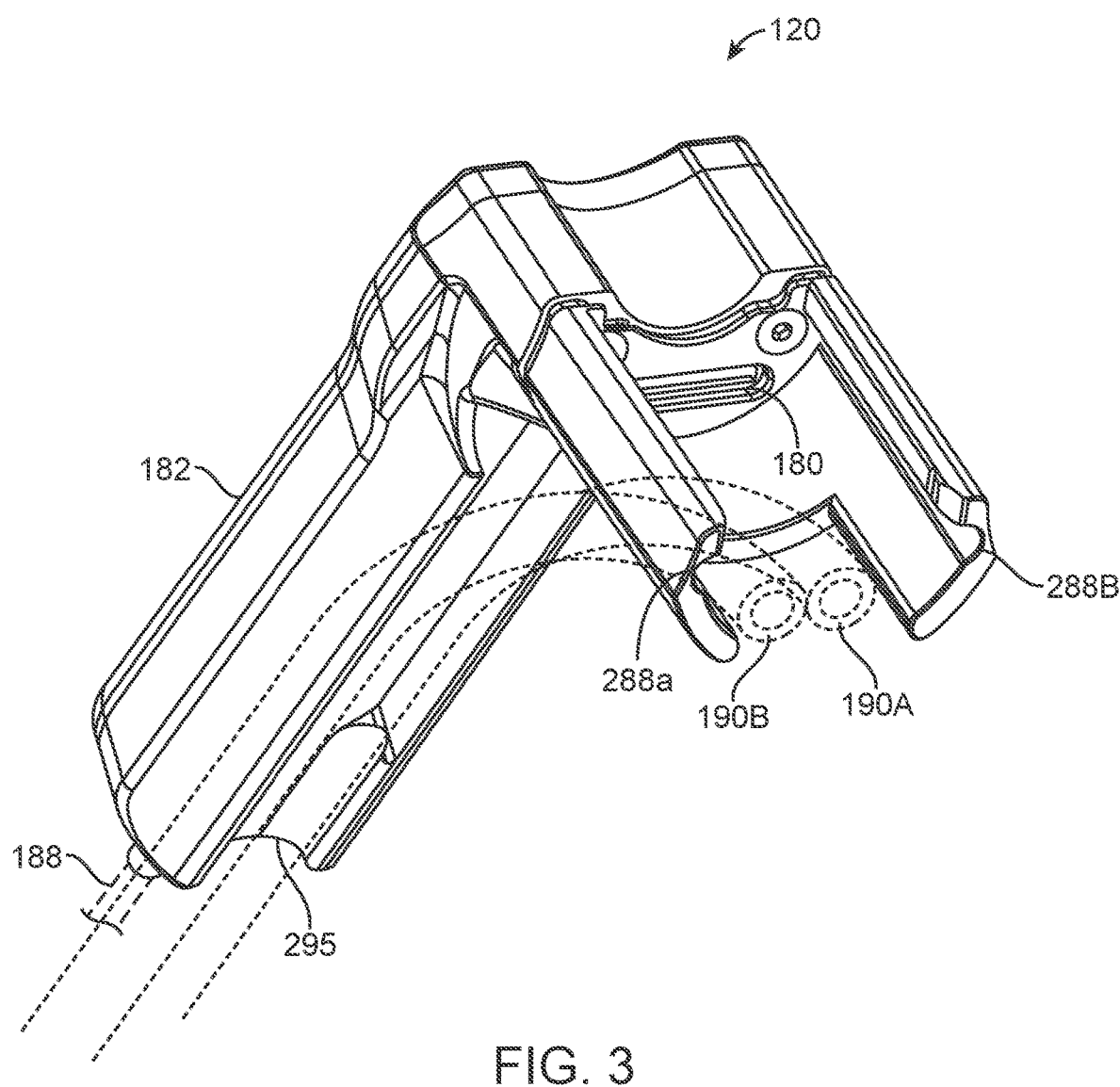
FIG. 3 is a view of a handle component, which shows electrical connector that interfaces with a projecting electrical connector of a hub of an endoscope component.

Now referring to FIGS. 2B and 3, it can be seen that the handle component 120 has an angled pistol grip portion 182 with an axis 184 that is angled from 10° to 90° away from the longitudinal axis 166 of the endoscope's proximal shaft portion 165. The grip portion 182 includes a control pad 122 that carries actuator buttons for operating all the functions of the treatment system, for example, including (i) operating the fluid management system 105, (ii) capturing images or videos from sensor 128, (iii) adjusting light intensity from the LEDs 244A and 244B, etc. The interior of the handle component 120 also can carry an image processor. or such an image processor may be located in the control unit or base unit 118 shown in FIG. 1A.

FIG. 3 is a view of the handle component 120 from a different angle, which shows the electrical connector 180 that interfaces with the projecting electrical connector 178 of the hub 176 of the endoscope component 125. FIG. 3 further shows receiving channels 288a and 288b that receive projecting rail elements 290a and 290b of the endoscope hub 176 as can be seen in FIG. 2B. In FIG. 3, it also can be seen that the grip portion 182 has a recessed channel 295 therein that is adapted to receive and lock in place the inflow and outflow tubing 190A and 190B so as to integrate the tubing set with the pistol grip 182 during use. This feature is important so that the inflow and outflow tubing will not interfere with operation of the endoscope component 125 or the resecting device 110 introduced through the working channel 175 as will be described in more detail below.

Figure 4:
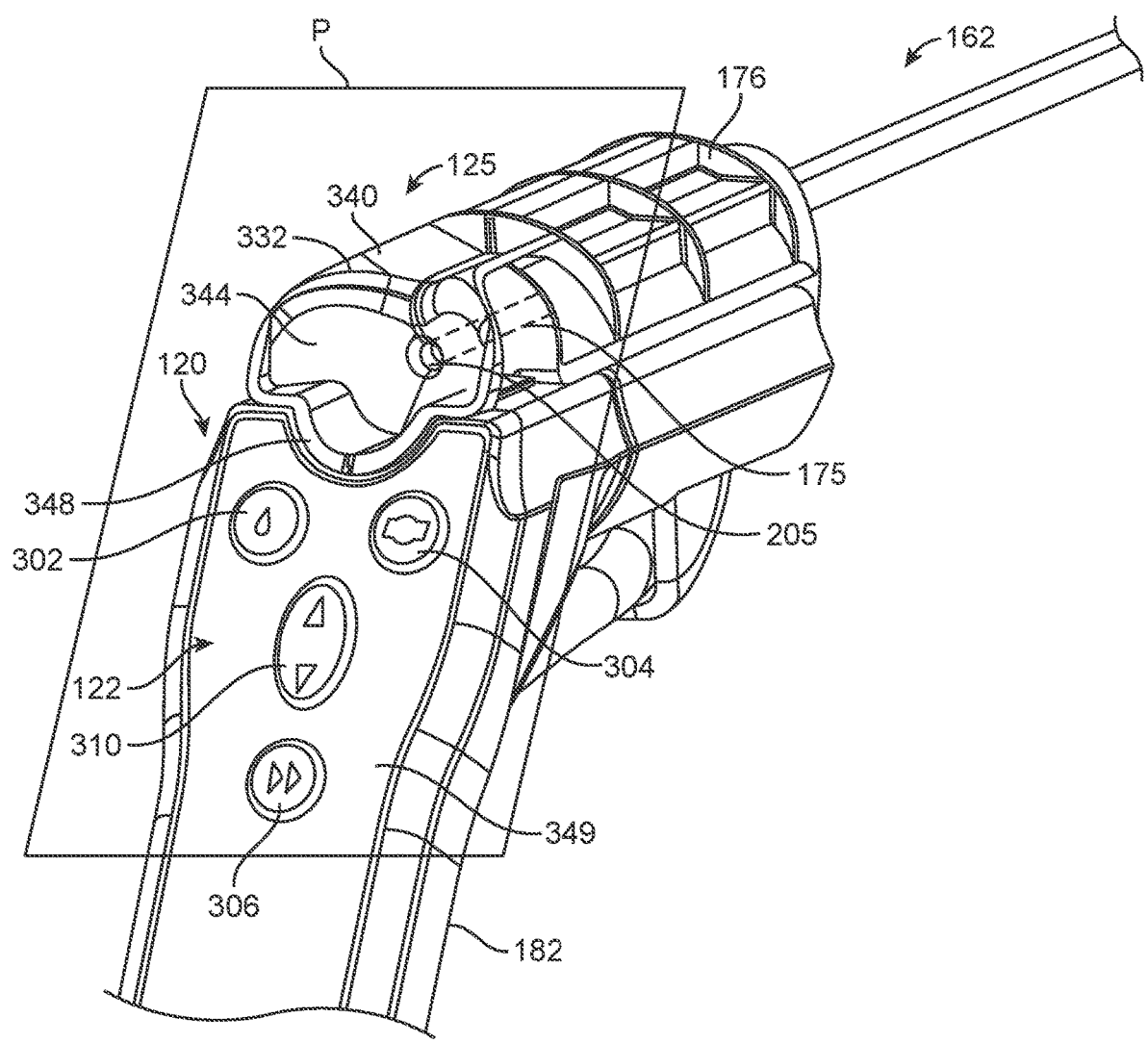
FIG. 4 is a perspective view of the endoscopic viewing system of FIG. 2A showing a finger-actuated control panel.

Now turning to FIG. 4, the enlarged view of the assembled handle component 120 and endoscope component 125 shows the control pad 122 with four actuator buttons or switches, which are adapted to operate the system. In one variation, actuator 302 is adapted for turning on and off irrigation, or in other words actuating the fluid management system 105 as will be described further below. Actuator 304 is adapted for image or video capture. In a variation, momentary pressing the actuator 304 will capture a single image and longer pressure on the actuator will operate a video recording.

Actuator or scrolling button 306 has a scrolling function, wherein pressing the scrolling button 306 will cycle through various subsystems that then can be further adjusted by the central button or up/down actuator 310, which is adapted for increasing, decreasing or otherwise changing an operating parameter of any selected subsystem. In one example, the scrolling button 306 can be actuated to cycle through the following subsystems and features: (i) fluid inflow/outflow rate from the fluid management system 105; (ii) the set pressure, which is to be maintained by fluid management system 105; (iii) fluid deficit alarm, which is calculated by the fluid management system 105; (iv) optional selection of still image capture or video capture, and (v) LED light intensity. Then, the physician can activate the central up/down actuator 310 to adjust an operating parameter of the selected subsystem. As will be described further below, the selection of subsystems as well as the real-time operating parameters of each subsystem will be displayed on a video monitor or display 320 as shown in FIG. 1A. Thus, it can be understood that the physician may operate the scrolling button 306 to scroll through and select any subsystem or feature while observing such as selection on the display 320, and then actuate the up/down actuator 310 can adjust an operating parameter, which also can be observed on the display 320.

In another aspect of the invention, the controller 115 includes a control algorithm for operating the control pad 122, which provides a jump back to a default condition after the scroll button or actuator 306 has been used by the physician. For example, there is a default condition in which a selected subsystem is actuatable by the central up/down actuator 310. In one variation, the default subsystem is the fluid inflow/outflow rate, which may be the most commonly used subsystems that will be actuated by the physician to control fluid flow into and out of the working space. Thereafter, as described above, the physician may use the scrolling button 306 to select another subsystem for adjustment of an operating parameter. If, however, the physician does not continue to scroll between the various subsystems for a predetermined amount of time, then the control algorithm will jump back to the default subsystem, which may be the fluid inflow/outflow rate. The predetermined amount of time, or timeout, with the control algorithm to jump back to the default condition may be anywhere from 1 second to 10 seconds, more often between 2 seconds and 5 seconds.

Figure 5:
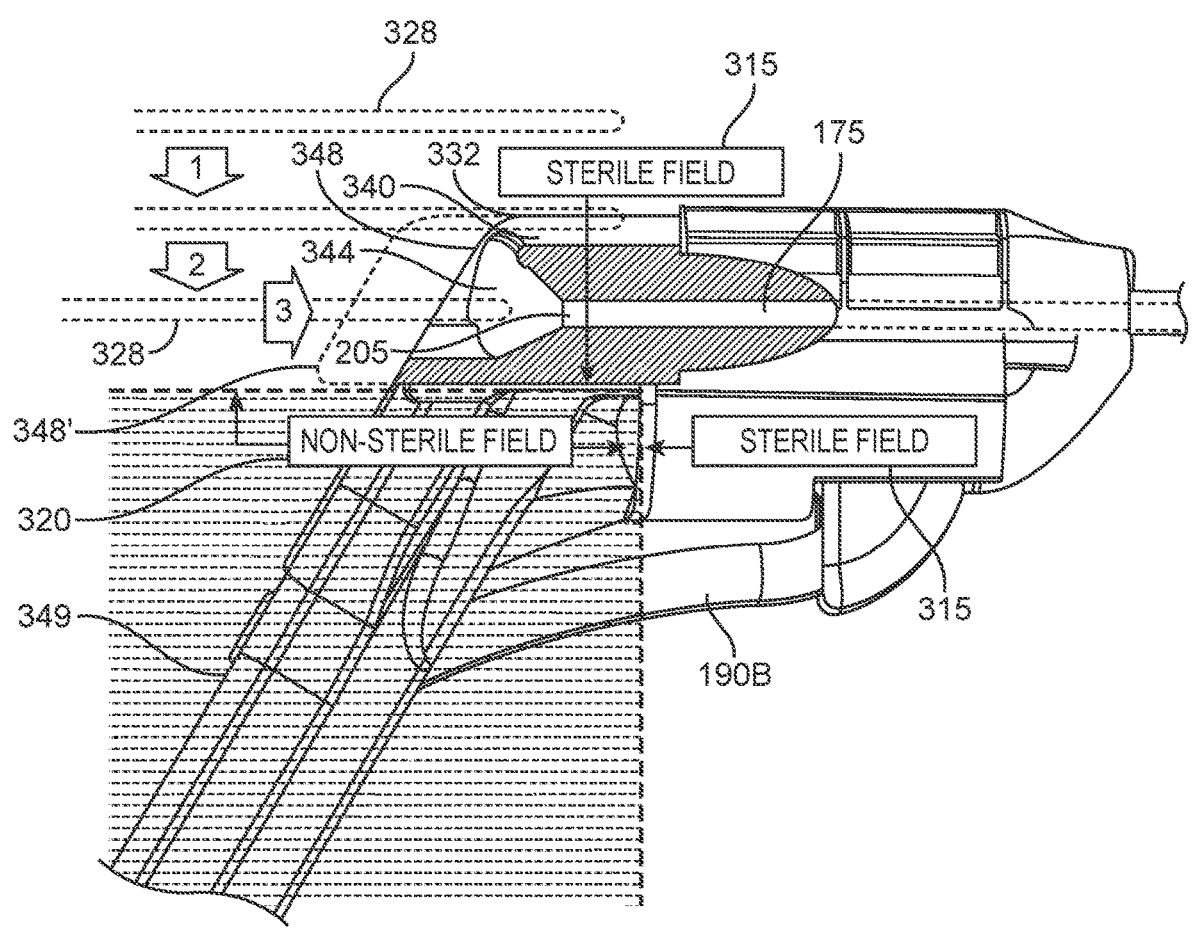
FIG. 5 is a cut-away side view of the endoscopic viewing system of FIG. 2A showing sterile and non-sterile fields of the components.

Now turning to FIG. 5, a schematic side view of the assembly of the handle component 120 with endoscope component 125 as shown to illustrate the sterile field 315 and the non-sterile field 320 relative to the endoscope assembly. As can be understood, the disposable endoscope component 125 is sterilized and the physician or nurse would remove the component 125 from sterile packaging, which would then define a sterile field 315. The endoscope component 125 then would be mated with the handle component 120, which defines the non-sterile field 320. In other variations (not shown), a plastic film or other plastic housing with the beast zero could cover the handle portion 120. FIG. 5 further illustrates a method that would be employed by the physician to insert an elongated tool shaft 328 into the working channel 175 in a manner that would ensure the sterility of the tool shaft 328. As can be seen in FIGS. 2A, 2B, 4 and 5, the superior surface 332 of the hub 176 includes a trough or recessed saddle 340 in which the physician can initiate contact with the tool shaft 328, which is indicated by an arrow in FIG. 5 and is numbered as step 1. Thereafter, as indicated by an arrow as step 2, the tool shaft 328 can be guided downward from the saddle 340 into the cone-shaped recess 344 in hub 176, which tapers distally to transition into the open proximal end 205 of the working channel 175. Thereafter, the physician can move the tool shaft 328 axially over the surface of the cone-shaped recess 340 and into and through the working channel 175. By using this method, the physician can be assured that the tool shaft 328 will not contact the non-sterile field 320. In FIGS. 4 and 5, it can be seen that the proximal slanted surface 342 of the hub 176 is substantially in the same plane P (FIG. 4) as the surface 349 of the angled grip portion 182. It should be appreciated that a slanted surface 342' of the hub 176 can be provided in a plane outward from the surface 349 of the grip 182 to provide further assurance that the tool shaft 328 will not contact the non-sterile field 320.

Base Unit and Fluid Management System

Figure 10:
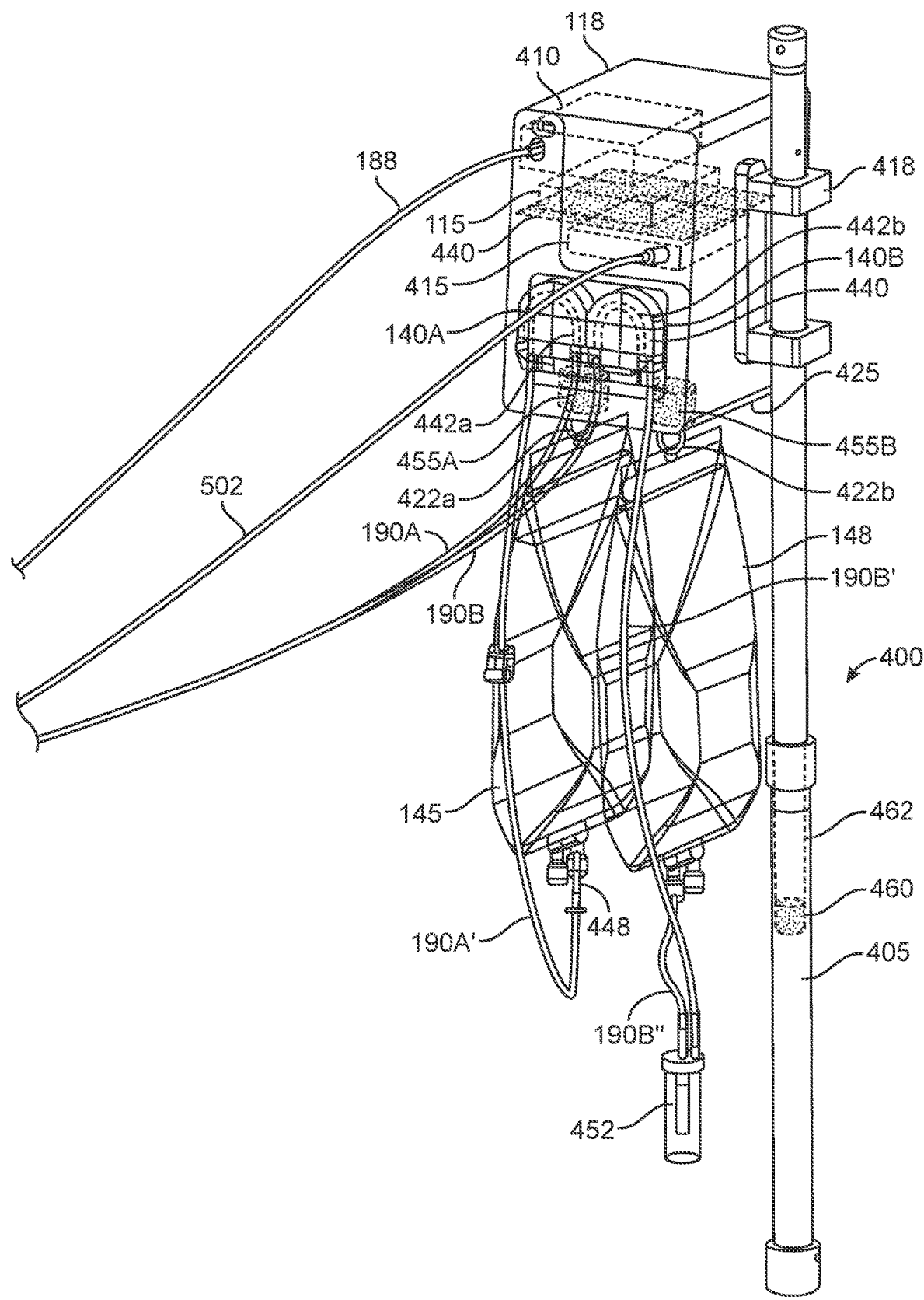
FIG. 10 is a perspective view of components of the fluid management system of FIG. 1A.

Now turning to FIGS. 1A and 10, the fluid management system 105 can be described in more detail. A rolling stand assembly 400 is provided, which includes a base 402 with wheels 404 and a vertical pole assembly indicated at 405. The video display 320 is mounted at the top of the pole assembly 405. A controller base unit or base station 118 is attached to the pole assembly 405, which comprises a housing containing the system controller 115, a video processor 410 and a 3-phase motor controller/power supply 415 for the resecting device 110 in this motor drive. Further, the base unit 118 carries the inflow and outflow peristaltic pumps 140A and 140B. The controller 115, as the term is used herein, includes processors or controller components for operating the fluid management system 105, the resecting device 110 and all aspects of the endoscopic viewing system 100. The base unit 118 also contains power supplies from the resecting device 110, the fluid management system 105 and the endoscopic viewing system 100.

As can be seen in FIG. 10, the base unit 118 is carried by a bracket 418 that secures the unit to the pole assembly 405. A fluid source, such as a 1-liter saline bag 145 is hung from a first hook 422a on the inferior surface 424 of the base unit 118. Further, another saline bag or collection reservoir 148 hangs from a second hook 422b on the inferior surface 425 of the base unit 118 for collecting fluid outflows.

FIGS. 1B and 10 further show a cassette 440 that carries first and second tubing loops 442a and 442b that are adapted to engage the roller assemblies of inflow and outflow pumps 140A and 140B. The cassette 440 shown in FIG. 11 includes a transducer membrane 444 (FIG. 1B) as is known in the art for interfacing with a pressure sensor and the surface of the control unit 118 that is engaged after the cassette 440 is locked in place.

In FIGS. 1A and 10, it can be seen that the inflow pump 140A pumps fluid through inflow tubing 190A to the endoscopic viewing component 100. FIG. 10 illustrates that a portion of the inflow tubing indicated at 190A' extends from the fluid source 145 to the tubing loop 442a in the cassette 440 that engages the inflow peristaltic pump 140A. The proximal end 448 of the inflow tubing portion 190A' as a spike for spiking the saline bag or fluid source 145 as is known in the art.

In FIGS. 1A and 10, it can be further seen that the outflow tubing 190B extends from the endoscopic viewing system 100 to the tubing loop 442b in the cassette 440 that engages the outflow peristaltic pump 140B. Beyond the tubing loop 445b in the cassette 440, an outflow tubing portion indicated at 190B' drops downward to a tissue trap 452 where tissue chips are filtered from the fluid outflow in collected. A second outflow tubing portion indicated that 190B" then extends upward to the collection reservoir 148.

Referring again to FIG. 10, the system includes at least one load sensor for providing weight signals to the controller indicating either the weight of the fluid in the inflow source 145 or the weight of the fluid in the collection reservoir 148 or the weight of the combined fluid inflow source 145 and collection reservoir 148. In one variation shown in FIG. 10, the first load cell 455a is shown with weighs fluid inflow source 145 in the second load cell 455b weighs the fluid collection reservoir. The controller 15 then can receive signals from the two load cells 455a and 455b to calculate the fluid loss. Further, the signal can be provided when a certain predetermined fluid loss has been observed. Also, the controller 115 can provide an alarm signal when the load cell 455a, which weighs the fluid source 145, determines that the fluid source is rated at a lower level, which may indicate that an additional saline bag should be connected to the fluid management system.

Still referring to FIG. 10, in another variation, the weight management system can use a load cell 460 and the pole assembly 405 wherein telescoping shaft 462 can carry the weight of both the fluid inflow source 145 in the collection reservoir 148 and continues to weigh the assembly in order to calculate the fluid deficit.

In another aspect of the invention, referring to FIG. 10, the base unit 118 is designed for use in a physician's office in therefore should be compact. In one variation the height of the base unit 118 is less than 18 inches, the width is less than 12 inches and the depth is less than 12 inches. Further, it has been found that the electrical interference caused by the 3-phase motor controller/power source 415 controller is substantial in the sensitivity of the video processor 410 is significant. Therefore, extensive electromagnetic shielding or EM shielding 488 is required between the 3-phase motor controller/power source and the video processor 410. In general, one aspect of the invention comprises providing a video processor within less than 12 inches from a three-phase motor power source and controller. In other variations, video processor is less than 8 inches, or less than 6 inches from the 3-phase motor controller/power source.

In general, as shown in FIG. 10, the base unit 118 includes a fluid management system 105 including inflow and outflow peristaltic pumps 140A and 140B, a cassette 440 carrying inflow and outflow tubing loops for engaging the inflow and outflow pumps, a coupled to the base unit 118 are a fluid source 145 comprising a first saline bag and a collection reservoir 148 comprising second saline bag. Further, the base unit 118 carries at least one load sensor intermediate the base unit housing in the first and second saline bag or weighing either or both of the first and second saline bags. A digital readout of the weight of either or both of the saline bags is provided on the monitor 320 (FIG. 1A) for observation in the recording by the physician or nurse. By this means, the fluid deficit can be calculated.

In another variation, the inflow and outflow pumps of the fluid management system utilize encoder-type motors, which can send signals relating to rotation to the controller 115. By this means, the controller 115 can calculate the volume of fluid inflows provided by a pump 140A into the working space in the patient's body. Thus, fluid inflows can be calculated either by a load cell or by signals from an encoder-type motor to the controller 115.

Tissue Resecting Device

Figure 11:
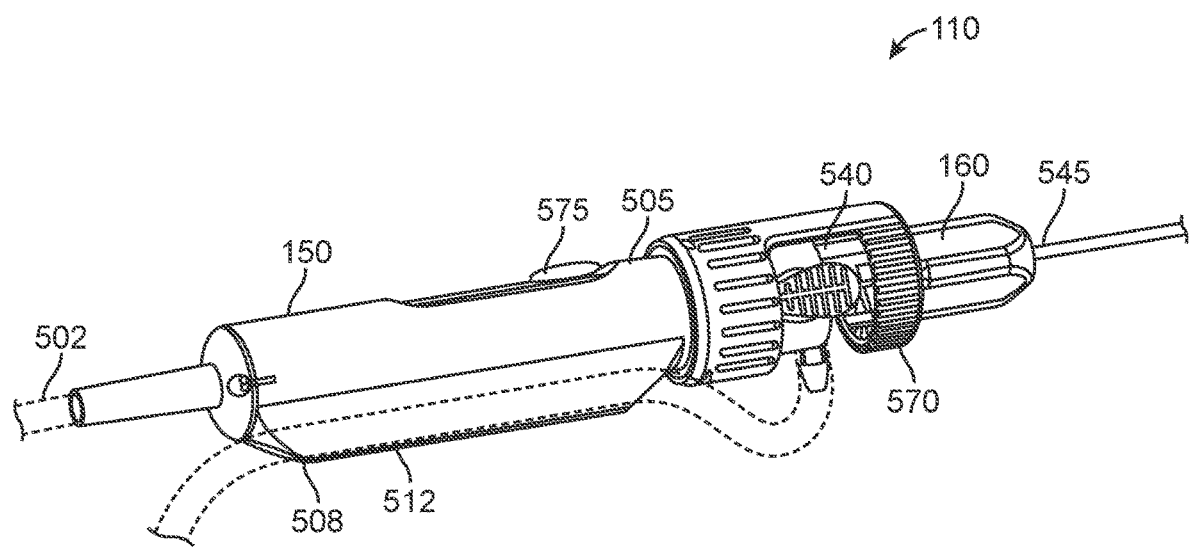
FIG. 11 is a perspective view of the handle portion of the resecting device of FIG. 1A showing the re-usable handpiece in the hub of the cutting component.
Figure 12:
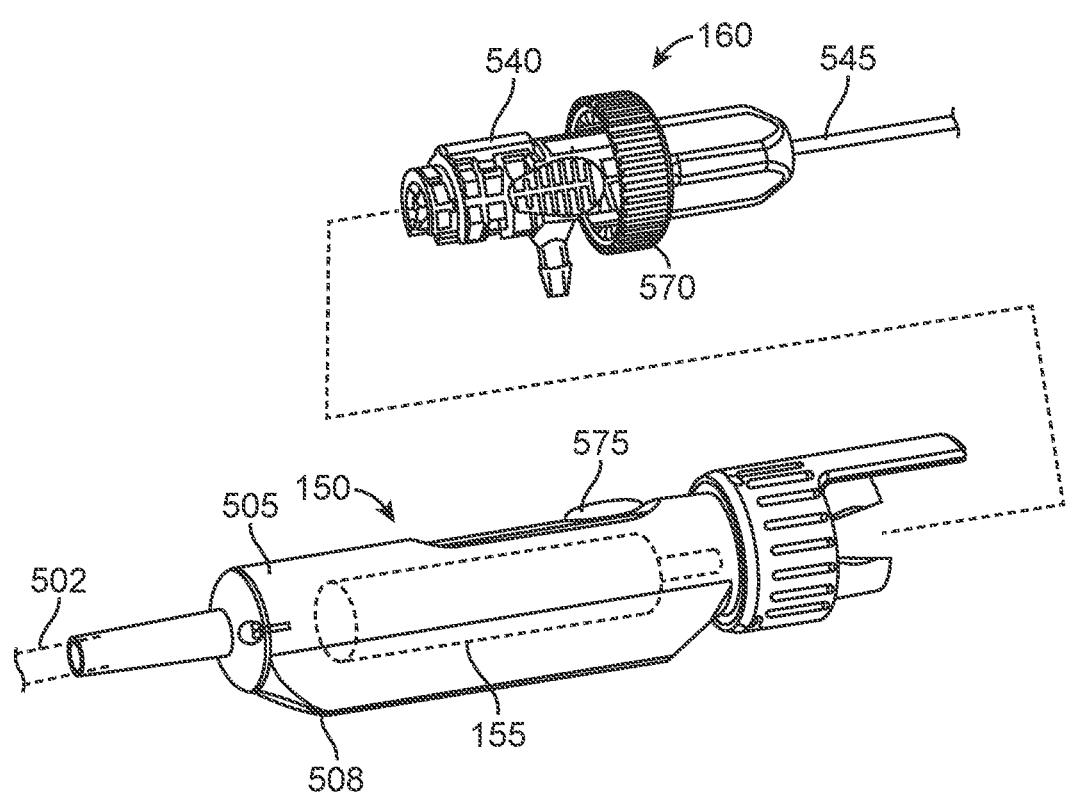
FIG. 12 is a view in the resecting device of FIG. 11 with the cutting component detached from the handpiece.

Now referring to FIGS. 1A, 11 and 12, the tissue resection device 110 comprises a re-usable handpiece 150 that carries a motor drive 155 together with the detachable cutting component 160. An electrical power cable 502 extends from the handpiece 150 to a 3-phase motor controller/power supply in the base unit 118. As can be seen in FIG. 11, the handpiece 150 has a housing 505 with a channel 508 in a lower portion thereof to receive and lock therein the outflow tubing portion indicated at 512. In FIG. 1A, it can be seen that outflow tubing 512 extends to a branch connector 515 that couples tubing 512 to the outflow tubing 190B extending back to the outflow peristaltic pump 140B in the base unit 118. The outflow tubing 512 as shown in FIG. 1A is a pinch valve 518 for closing off the outflow tubing 512. In FIG. 1A, it can be understood that the primary outflow tubing 190A extends to the endoscopic viewing system 100 through the branch connector 515 into tubing portion 520 to the hub 176 of the endoscope component 125 as described above. Thus, the endoscopic viewing assembly 100 can be used for both inflows and outflows during insertion of the endoscope shaft assembly 162 into the patient, with the pinch valve 518 closing off the outflow tubing 512 since the resecting device 110 is not yet in use (FIG. 1A). After the endoscope shaft assembly 162 has been navigated to a working space in a patient's body, and the resecting device 110 has been introduced through the working channel 175 of the endoscope component 125, the pinch valve 518 can be opened so that fluid outflows are provided through the resecting device 110 rather than through the working channel 175 of the endoscope component 125.

Figure 13:
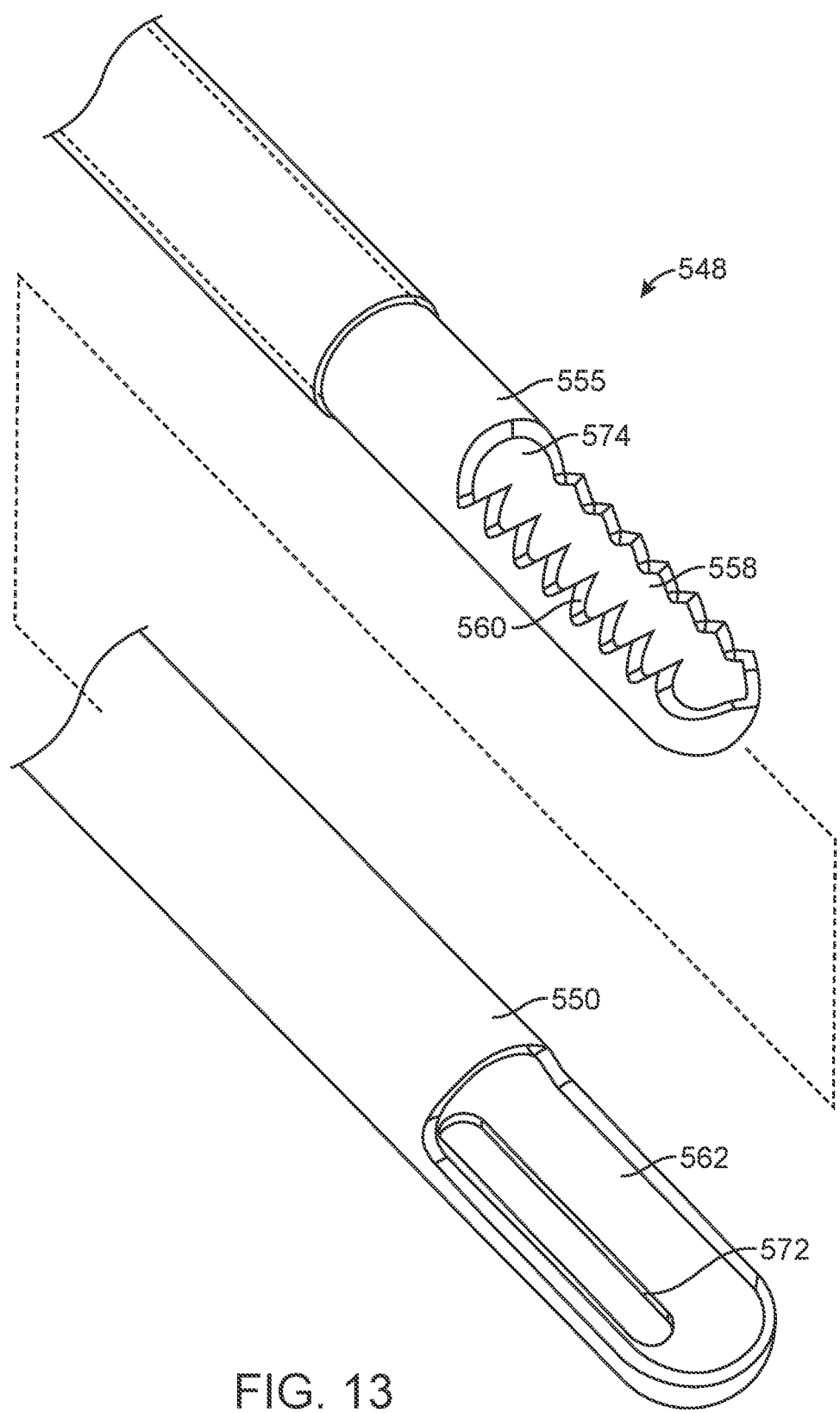
FIG. 13 is an enlarged perspective view of the working end of the resecting device of FIGS. 1A and 11 with the inner sleeve separated from the outer sleeve showing an aperture arrangement in the outer sleeve.

Now turning to FIG. 12, it can be seen that the cutting component 160 has a proximal hub 540 that is adapted for detachably coupling to the handle 150. An elongated shaft assembly 545 extends distally from the hub 540 to a working end 548 (FIG. 1A). In one variation, elongated shaft assembly 545 comprises an outer sleeve 550 with a distal window 552 and a rotating inner sleeve 555 with a window 558 (FIG. 13). Such a type of tubular cutter is known in the art wherein the rotating inner sleeve 555 cuts tissue that interfaces with window 552 in the outer sleeve 550 as the inner sleeve window 558 with teeth 560 rotates at high speed.

As can be seen in FIGS. 11 and 12, the hub 540 of the resecting component 160 is coupled to a rotating collar 570, which is fixed to the shaft assembly 545 so that the physician can rotate the shaft assembly 545 and working end 548 to any rotational orientation for cutting tissue while maintaining the handle 150 in an upright position. The handle 150 includes an actuator button 575 for actuating the motor drive 155 to rotate the inner sleeve 555 relative to the outer sleeve 550 to thereby cut tissue.

Referring to FIG. 12, the tissue resecting device 110 can have a shaft assembly 5456 with a diameter ranging from 2 mm to 6 mm, in is more often between 3 mm and 5 mm. The shaft 545 has a diameter and length for cooperating with the working channel 175 of the endoscopic viewing system 100 as shown in FIG. 1A.

Now turning to FIG. 13, the distal working end 548 of the cutting component, and more particularly, the outer and inner sleeves, 550 and 555, are shown separated to show particular features that correspond to the invention. In FIG. 13, it can be seen that the outer sleeve 550 is in has an aperture arrangement or opening 572 in the surface that opposes the window 562. Typically, in a high-speed rotating tubular cutter that is used in hysteroscopy with a fluid management system, the motor controller includes algorithms for stopping rotation of the inner sleeve 555 relative to the outer sleeve 550 so that the windows 558 and 562 are aligned when the inner sleeve 555 stopped rotating. In such prior art devices, various sensors and mechanisms have been developed to stop rotation of the inner sleeve 555 in a predetermined position with the inner and outer windows 558, 562 being oriented to be at least partially aligned and open. Such algorithms are complex and may not function reliably in all operating environments. The reason for needing such a controller algorithm for stopping rotation of the inner sleeve 555 with windows 558 and 562 aligned is to ensure that the fluid management system continues to operate to maintain a set pressure in the body cavity when the resecting device is (i) operating at high speed or (ii) when the resecting device is paused in operation. The control algorithms of the fluid management system for maintaining a set pressure in a body cavity typically use a PID controller or a feedback control system as is known in the art. During operation of a resecting device with a rotating inner sleeve as shown in FIG. 13, the fluid management system controller can continuously monitor fluid outflows through the windows 558 and 562 when aligned since the sleeves are only in a window-closed position for a very brief interval as the inner sleeve 555 rotates. The stop algorithm is then used to stop rotation of the inner sleeve 555 in a window-open position and the controller again will monitor continuous fluid flows through the system to maintain the set pressure. However, if the inner sleeve 555 stopped rotating in a window-closed position, the actual pressure in the body cavity would immediately increase and the control algorithm could react by slowing or stopping the pumps but with no fluid outflows in the window-closed position, the PID controller could not operate, which could increase actual pressure in the body cavity to an unsafe level or cause significant fluctuations in pressure in the working space when the resecting device is re-activated to provide fluid outflows.

In one aspect of the present invention, an opening or aperture arrangement 572 is disposed in a wall of outer sleeve 550 opposing the open window 562. In general, the opening 572 allows for outflows through the lumen 574 in the inner sleeve when it stops in the window closed position. Thus, providing an outflow opening 572 in the outer sleeve was the fluid management control system and PID feedback controller to operate and maintain the set pressure no matter whether the inner sleeve 555 is stopped in a window-open position or window-closed position or any intermediate position. In order to provide adequate flow through the outflow opening 572 in the window-closed position, it has been found that the area of opening 572 should be at least 10% of the area of window 558 in outer sleeve and more often at least 20% of the area of the window 558 in outer sleeve 555. In a variation, the area of opening 572 is at least 30% of the area of window 558 in outer sleeve 555. In FIG. 13, the opening 572 in the outer sleeve 550 is shown as a single elongated shape, but it should be appreciated that the opening can comprise a plurality of openings, which can be any shape such as elongated slot or slots, an oval shape, round openings or the like.

Figure 14A:
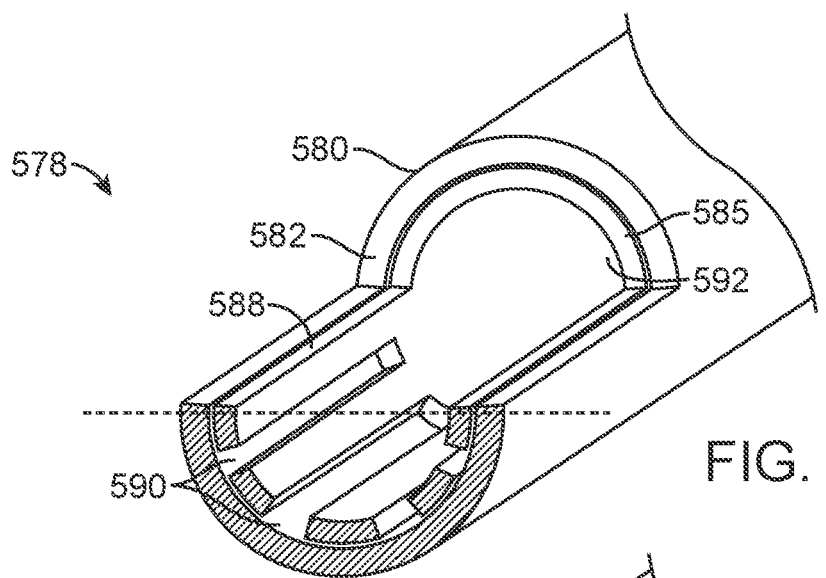
FIG. 14A is a schematic view of a working end of another resection device similar to that of FIGS. 1A and 11 showing an inner sleeve with a cutting window and opposing apertures in a first window-open position.
Figure 14B:
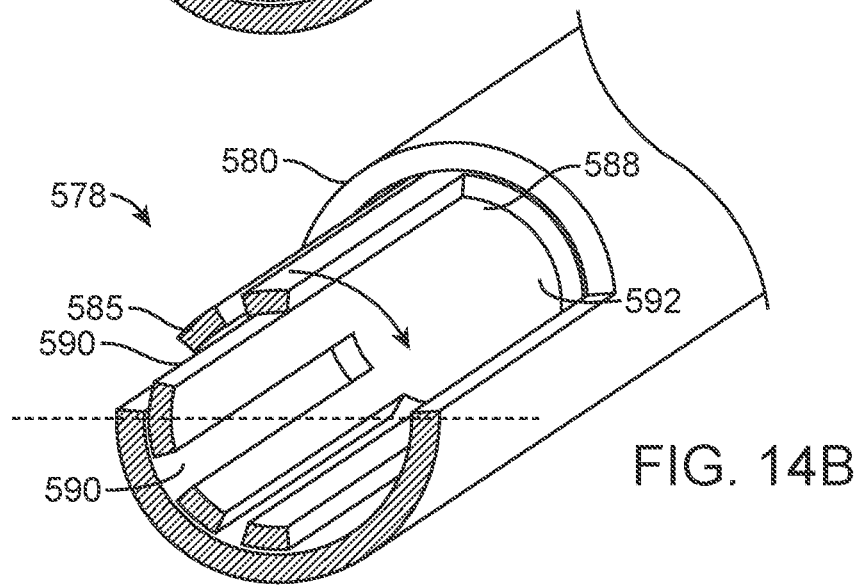
FIG. 14B is another view similar to that of FIG. 14A showing the inner sleeve and cutting window in a second position.
Figure 14C:
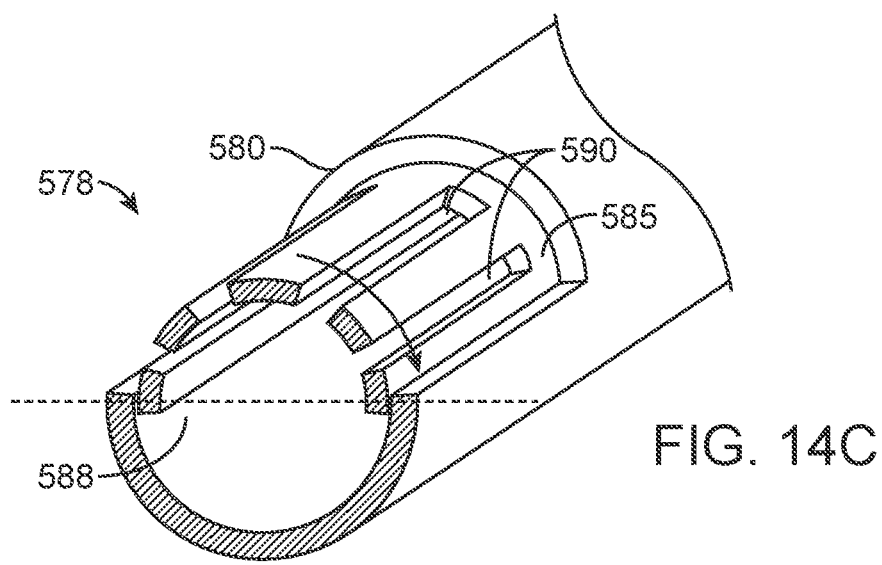
FIG. 14C is a view similar to that of FIGS. 14A-14B showing the inner sleeve and cutting window in a third window-closed position.

Now turning to FIGS. 14A to 14C, another variation of working end 578 is shown that is adapted to solve the same problem as the variation of FIG. 13. FIGS. 14A-14C are schematic views of a working end 578 of a tubular cutter with the outer sleeve 580 having window 582 therein. The inner sleeve 585 has cutting window 588 that, for convenience, is shown without cutting teeth. In this variation, it can be seen that inner sleeve 585 has a plurality of outflow openings 590 therein that extend longitudinally and are spaced apart around a wall of the inner sleeve 585 opposing window 588. In this variation, the aperture arrangement can have from 1 to 20 or more openings. Again, it can be seen in FIG. 14C that when the working end 578 is in the window-closed position, the outflow openings 590 will still allow for fluid outflows through the interior channel 592 of the inner sleeve 585 to ensure that the PID controller or other control system still can function properly since there is a fluid flow through the device. The area of the apertures or openings again is greater than 10% of the outer sleeve window, greater than 20% or greater than 30% of the area of the window 582 in the outer sleeve 580.

In another aspect of the invention, the resecting device 110 comprises a tubular cutter wherein a windowed inner sleeve rotates relative to the outer sleeve between window-open in window-closed positions, and wherein a cooperating fluid management system provides of fluid outflows through a central channel in the tubular cutter and wherein the fluid outflow in the window-closed position is at least 50% of the fluid outflow through the tubular cutter in the window-open position under the same fluid management settings. Again, the fluid outflows in the window-closed position are provided through at least one aperture or opening in either the outer sleeve, the inner sleeve or a combination of both the inner and outer sleeves.

In another aspect of the invention, a tissue resection system for resecting tissue in a fluid-filled working space comprises a working end comprising inner and outer sleeves having respective inner and outer cutting windows wherein the inner sleeve is adapted to rotate to provide window-open and window-closed positions, a controller operatively connected to a negative pressure source in communication with a flow channel having first cross-sectional area in the inner sleeve, an aperture arrangement in the surface of either the inner or outer sleeve opposing a respective inner or outer cutting window, and a PID control algorithm adapted to maintain a selected set pressure in the working space between 10 mmHg and 200 mmHg during at any angle of rotation of the inner sleeve relative to the outer sleeve. In this variation, the inner window, outer window and aperture arrangement define a combined open area for accommodating fluid outflows in response to the negative pressure source, and wherein said combined open area varies at each degree of 360° rotation of the inner sleeve relative to the outer sleeve, and wherein the minimum combined open area varies from the maximum combined open area during said 360° of rotation by a factor that does not impinge on continuous function the PID control algorithm to maintain said selected set pressure. In the above variation, the minimum combined open area varies from the maximum combined open area during said 360° of rotation by less than 50%. Often, the minimum combined open area varies from the maximum combined open area during said 360° of rotation by less than 40%, less than 30% or less than 20%.

In another aspect of the invention, the resecting device working end comprises inner and outer sleeves having respective inner and outer cutting windows, wherein the inner sleeve is adapted to rotate between window-open and window-closed positions, an aperture arrangement in the surface of the inner or outer sleeve opposing a respective inner or outer cutting window, and a controller operatively coupled to a negative pressure source connected to a flow channel in the inner sleeve for providing a fluid outflows from the fluid-filled working space through a combination of the inner window, outer window and aperture arrangement. At any selected rotational position of the inner sleeve relative to the outer sleeve, a controller utilizes a PID control algorithm for maintaining a set pressure in the fluid-filled working space wherein at any selected set pressure, the flow rate of said fluid outflows at any window-open or window-closed position varies less than 50%. Often, the flow rate varies by less than 40%, less than 30% or less than 20%.

In another aspect of the invention, the resecting device comprises a working end comprising inner and outer sleeves having respective inner and outer cutting windows, wherein the inner sleeve has an interior flow channel and is adapted to rotate between window-open and window-closed positions, an aperture arrangement in the surface of the inner or outer sleeve opposing a respective inner or outer cutting window wherein the flow channel has a first cross-sectional area and the combination of the inner window, outer window and aperture arrangement at a selected rotational position of the inner sleeve relative defines a minimum second cross-sectional area and wherein the ratio of the second cross-sectional area to the first cross-sectional area is at least 0.5:1. Often, the ratio of the second cross-sectional area to the first cross-sectional area is at least 0.6:1, at least 0.7:1 or at least 0.8:1.

Figure 15:
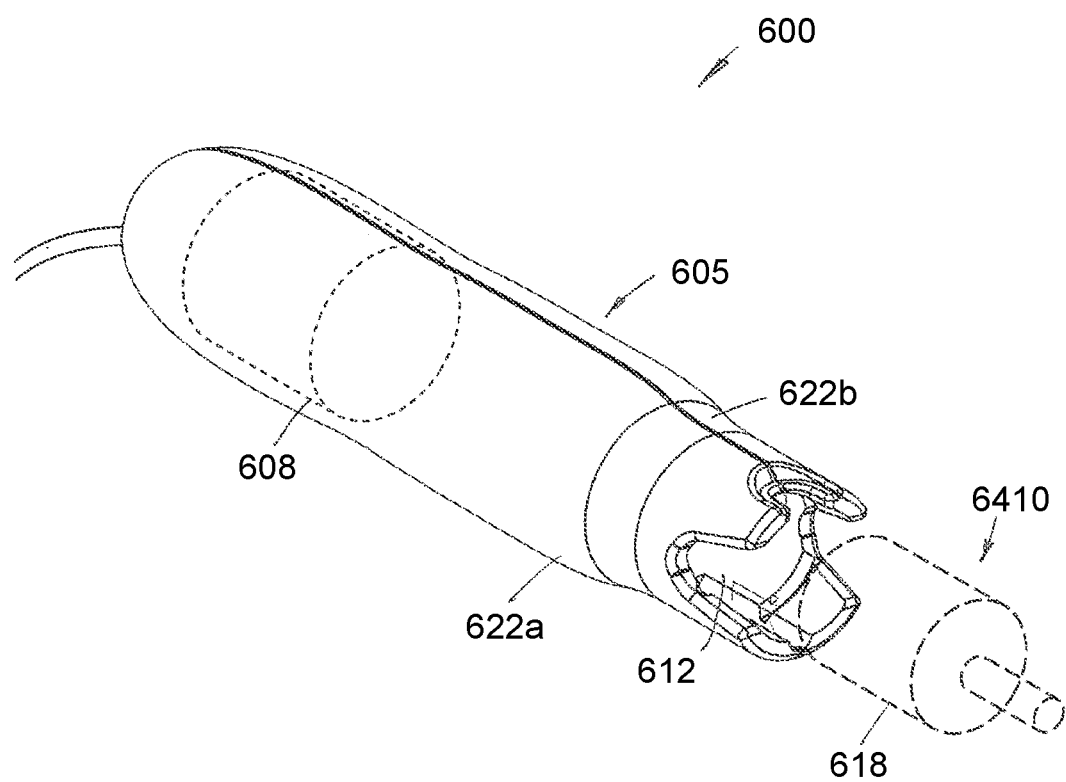
FIG. 15 is a perspective view of a single-use disposable or re-useable handle that carries a motor drive to which an elongated tubular cutting assembly or resection component can be detachably coupled.

Now turning to FIGS. 15 through 18B, another variation of resecting device 600 is shown wherein the handle or handpiece 605 and motor 608 are configured for single-use. The detachable elongated cutter assembly or component 610 is similar to that shown in FIGS. 1, 12 and 13. FIG. 15 shows the single-use handle 605, which is dimensioned for gripping with a human hand and has a distal channel 612 for receiving a hub 618 of the tubular cutter component 610. The handle 605 includes molded first and second sides 622a and 622b with a hollow interior that carries the motor 608 and a gear assembly for oscillating the inner sleeve cutting window relative to the outer sleeve window (see FIG. 13).

Figure 16:
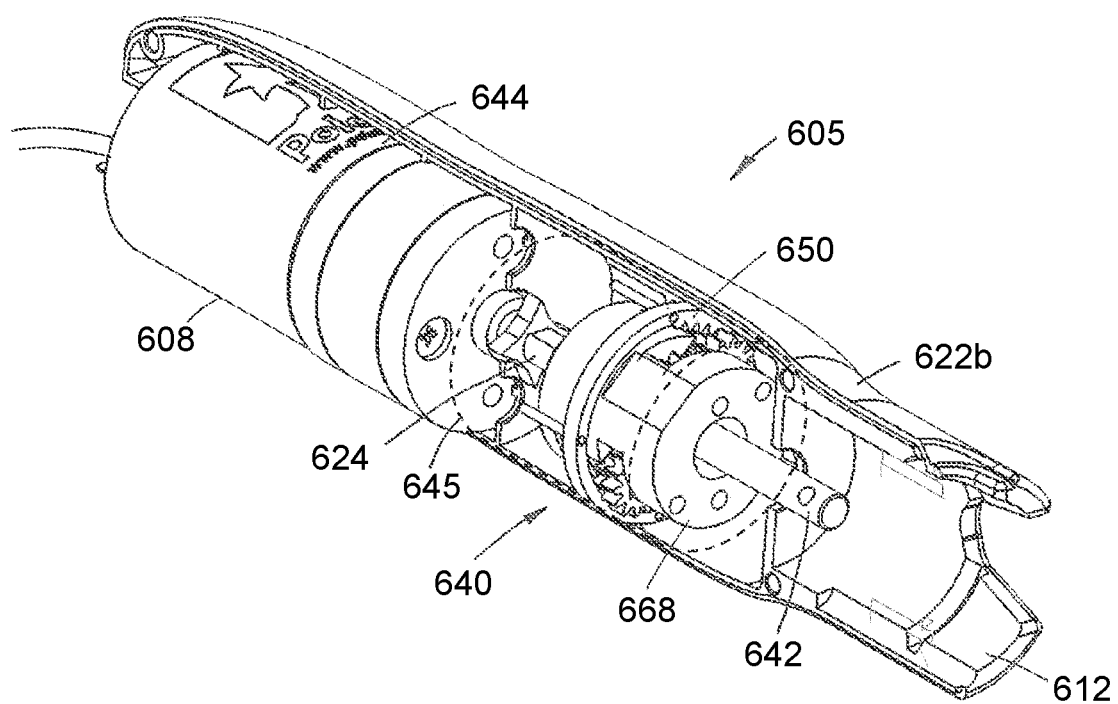
FIG. 16 is a perspective view of the handle of FIG. 15 with one side removed to show the motor and gear assembly that is configured for converting the unidirectional rotation of the motor shaft into an oscillating rotational movement of a tubular cutting member in the working end of the resection component.

FIG. 16 shows the handle 605 of FIG. 15 with a first side 622a of the exterior shell removed to show the motor drive 608 and the gear assembly. Of particular interest, the handle 605 carries an inexpensive, disposable DC electric motor 608 with drive shaft 624, which allows for its disposability. As is known in the art, sterilization of motor drive handles is complex and expensive. The cost of sterilization as well as the risks associated risks of infection from improperly sterilized devices makes disposable units less expensive than reusable units.

As is well known in the field of tissue resection, tubular rotational cutters work optimally when the inner rotating sleeve and cutting window oscillates, for example, with several revolutions in one rotational direction followed by a similar number of rotations in the opposite direction. Such oscillation provides improved cutting performance when compared with devices that rotate a cutting member in a single direction. In commercially available devices that provide an oscillating cutting member, three-phase motor are used, which are very expensive and thus require a robust handpiece, which is suitable for sterilization. Three-phase motors require high-power and also caused excessive heating of the handpiece as excessive energy is used to accelerate then decelerate and stop the cutter rotation and then reverse direction.

Figure 17:
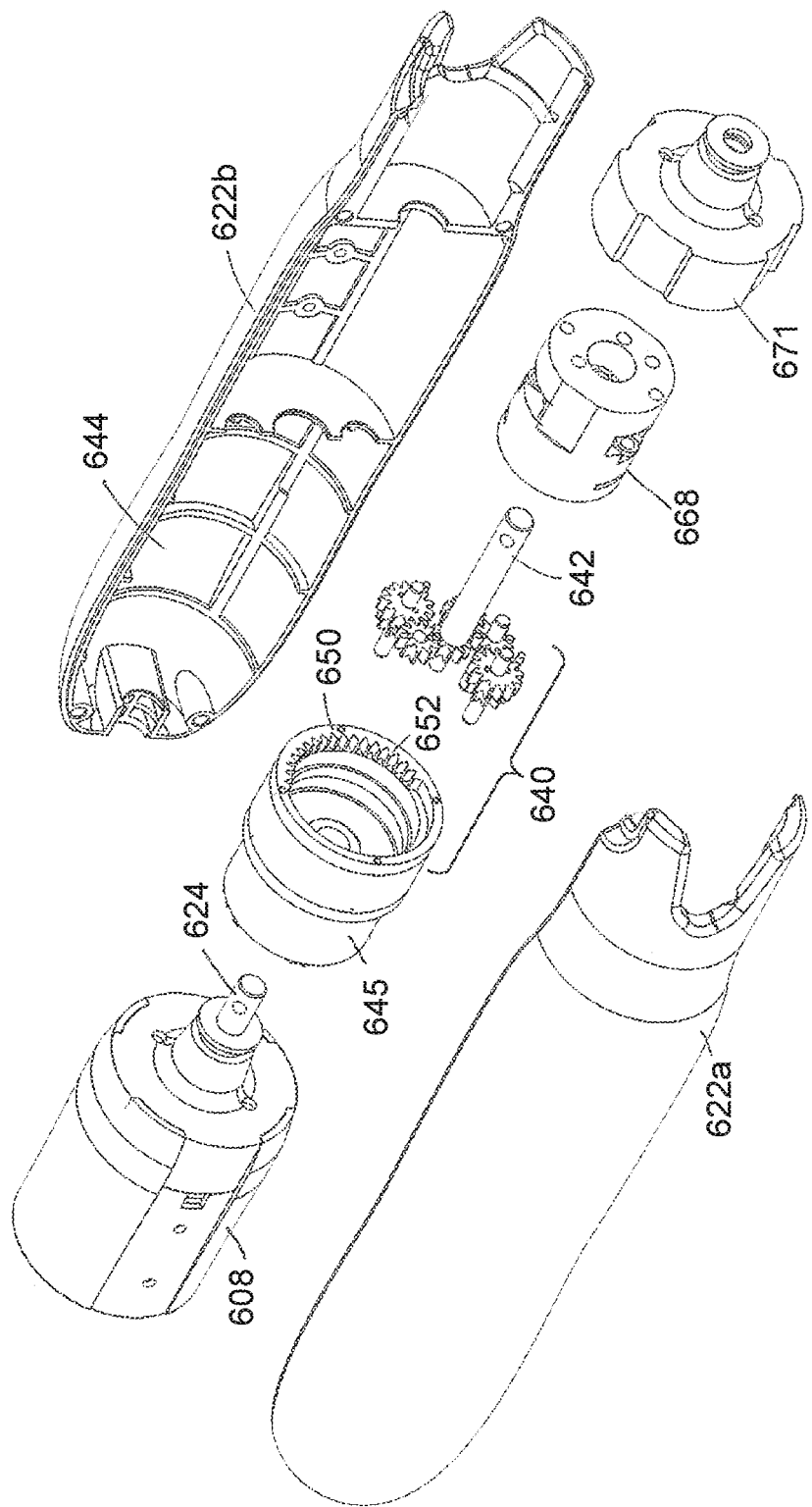
FIG. 17 is an exploded view of the components in the interior of the handle of FIG. 16 showing the motor and gear assembly.

Of particular interest, a resecting device of FIG. 16 corresponding to the invention comprises a single-use handpiece with an inexpensive DC motor adapted to rotate in a single direction together with a gear mechanism that converts the single direction of rotation of the motor drive shaft 624 to an oscillating rotation of the tubular cutting member at the working end of the device. FIGS. 16-17 show the gear mechanism or assembly 640 that accomplishes the conversion of continuous unidirectional rotation of the motor drive shaft 624 to oscillating rotation of the output shaft 642 of the gear assembly 640 and the inner sleeve cutting member 555 as shown in FIG. 13.

FIG. 17 is an exploded view of the components in the interior of handle 605 of FIG. 16 from which the gear mechanisms can be understood. As can be seen in FIG. 17, the DC motor 608 is located in the proximal end 644 of the handle 605. The motor 608 and its drive shaft 624 are coupled to rotating housing 645 that carries a partial ring gear 650. As will be described further below, the ring gear teeth 652 project inwardly and extend approximately 180° around the ring gear. Typically, the ring gear teeth 652 extend 1 to 4 teeth fewer than would be provided if the gear teeth extended a full 180°. As can also be seen in FIGS. 17 and 18A-18B, the gear assembly 640 includes five pinion gears 655A-655E that ultimately engage the central gear 660 that is fixed to the oscillating output shaft 642 that couples to the inner sleeve 555 (FIG. 13) of cutting component 610 (FIG. 15). The five pinion gears 655A-655E are carried in the pinion gear housing 668, which couples to distal housing cap 671.

Figure 18A:
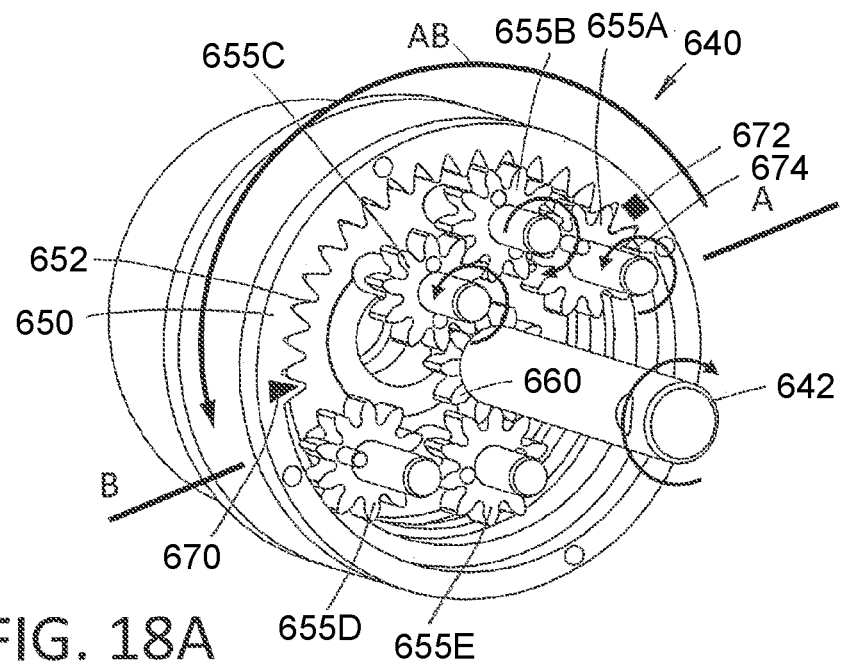
FIG. 18A is an enlarged perspective view of the gear assembly of FIGS. 16-17 showing a first position showing the arrangement of gears that can convert continuous rotation of an outer ring gear to an oscillating rotation of a central shaft coupled to a tubular cutting member; where rotation of the counter-clockwise of the ring gear in a first arc rotates the central shaft in a clockwise direction.
Figure 18B:
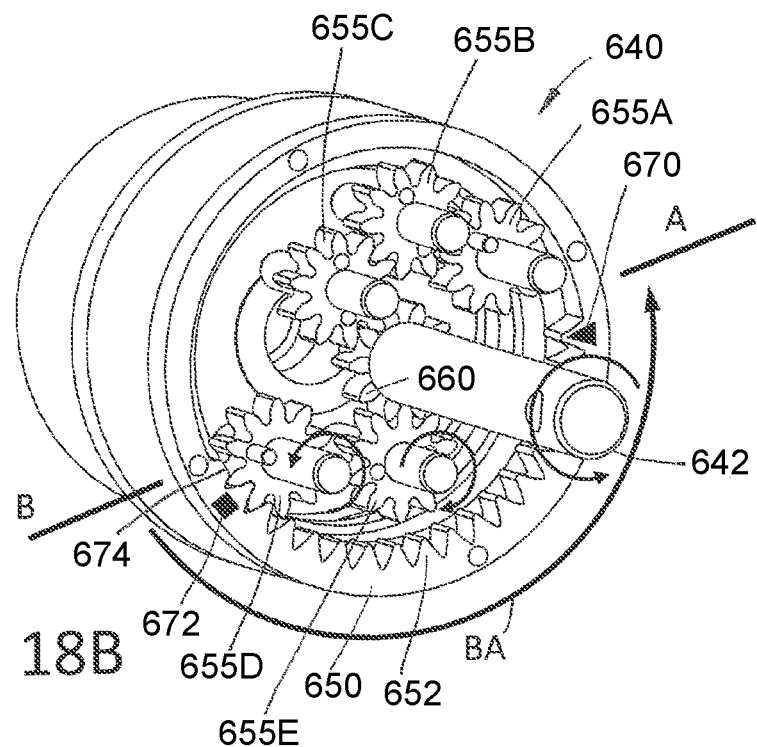
FIG. 18B is another view of the gear assembly of FIG. 18A in a second position wherein continued counter-clockwise rotation of the ring gear in a second arc rotates the central shaft in a counter-clockwise direction.

Now turning to FIGS. 18A-18B, enlarged views of the gear assembly 640 configured to oscillate the central shaft or output shaft 642 are shown separated from the other handle components to better illustrate the operation of the gears. In FIG. 18A, it can be seen that the outer ring gear 650 is in a first position after rotating counter-clockwise from point A toward point B in the arc indicated at AB. The ring gear 650 in this variation has 18 teeth indicated at 652 that extend around the inner surface of the ring gear somewhat less than 180°. For convenience, the first tooth 670 is marked with a black diamond and the 17th tooth 672 is marked with the black rectangle. The 18th tooth 674 is a partial tooth with a flattened top, which is needed for smooth meshing of the gears in 360° rotation of the ring gear 650 as can be understood after review of FIGS. 18A and 18B.

Thus, in FIG. 18A, it can be seen that ring gear 650 and more particularly the first tooth 670 with the black diamond mark has rotated close to 180° from point A toward point B. During this counter-clockwise rotation of the ring gear 650, the gear teeth 652 (teeth 1 through 18) have engaged and rotated pinion gear 655A in the counter-clockwise direction. Simultaneously, pinion gears 655A has engaged and rotated pinion gear 655B in a clockwise direction. Also simultaneously, pinion gear 655B has engaged and rotated pinion gear 655C in the counter-clockwise direction, which in turn engaged and rotated the central gear 660 and output shaft 642 in a clockwise direction for a first clockwise portion of an oscillation.

In FIG. 18A, it can be understood that gear teeth 17 and 18 (672, 674) of ring gear 650 are about to disengage pinion gear 655A and gear tooth 1 (670) and is about to engage pinion gear 655D. FIG. 18B shows the ring gear 650 rotated counter-clockwise about another 180° from point B back towards point A in arc AB, wherein the gear teeth 652 have rotated pinion gear 655D in the counter-clockwise direction. Simultaneously, pinion gear 655D has engaged and rotated pinion gear 655E in a clockwise direction, which in turn rotated the central gear 660 and output shaft 642 in a counter-clockwise direction. Thus, the second counter-clockwise portion of an oscillation is shown. In other words, the 360° rotation of ring gear 650 has caused an oscillating rotation of the central gear 660 and output shaft 642. As can further be seen in FIG. 18B, gear tooth 1 (670) is approaching pinion gear 655A, which will then repeat the sequence just described in the next 360° rotation of the ring gear. It has been found that high speed rotation of the ring gear 650 by the DC motor 608 (FIG. 16) it is highly durable, reliable and inexpensive.

It should be appreciated that by varying the dimensions or fineness of the teeth 652 of the ring gear 650 together with the diameters of the pinion gears, the oscillation of the central shaft or output shaft 642 can range from 1 to 8 shaft rotations for each 360° rotation of the ring gear 650. It should further be appreciated that gear mechanism 640 is adapted to maintain significant torque from the motor drive, which is the beneficial in cutting tissue. Further, it has been found that the gear mechanism 640 can operate at any suitable rotation speed, for example 100 RPM to 5000 RPM or more.

The configuration shown in FIGS. 18A and 18B is also referred to as a planetary gear system with ring gear 650 partially circumferentially surrounding a first set of planet gears 655A, 655B, 655C and a second set of planet gears 655D, 655E such that the ring gear engages either the first set of planetary gears or the second set of planetary gears to produce oscillating motion of the output shaft 642.

Figure 19:
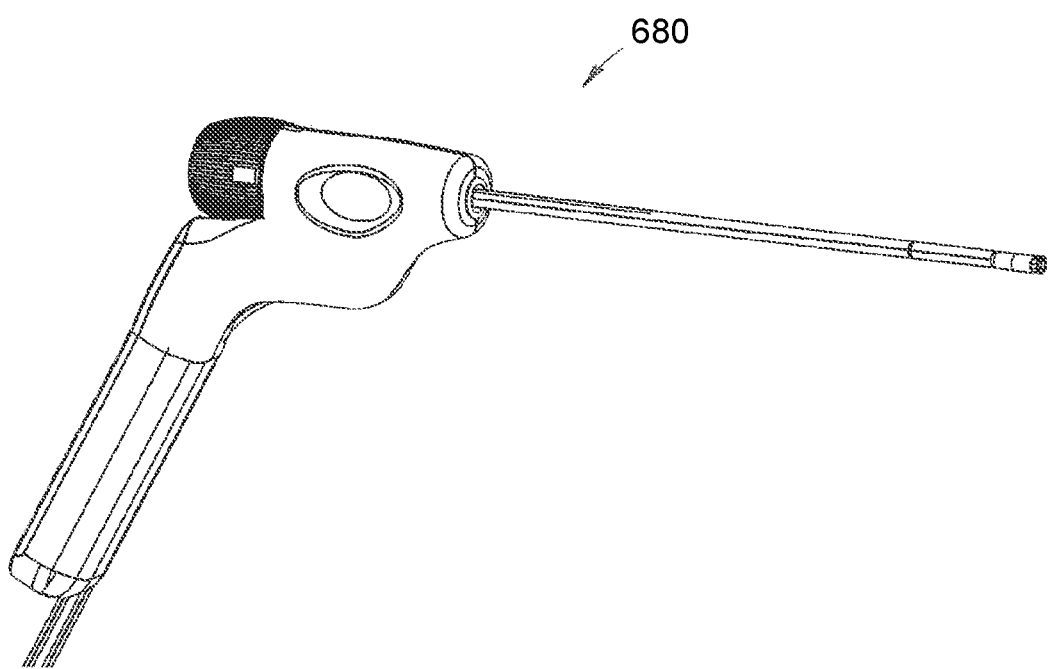
FIG. 19 is a perspective view of another endoscope similar to that of FIGS. 1A-9B except that the entire endoscopic viewing system is configured for single use and is disposable.

Now turning to FIG. 19, another variation of endoscope 680 is shown, which is similar to that described previously in FIGS. 1A to 9B in terms of all the functional components and aspects of the system. In the variation shown in FIG. 19, the endoscope differs in that the entire handle and endoscope assembly is configured for single-use and is disposable. In the previous embodiment of FIGS. 2A-5, the shaft portion of the endoscope is single-use and disposable wherein the grip portion in the actuator panel was reusable. Thus, disposable endoscope 680 of FIG. 19 corresponding to the invention comprises a single-use endoscope system that includes a handle coupled to an elongated shaft carrying an image sensor, wherein the handle carries system control or actuator components comprising at least an actuator for image capture, an actuator for controlling fluid flows from the fluid management system, and an actuator for controlling set pressure. Of particular interest, all of the aspects and features of the embodiments described above in FIGS. 1 through 9B can be included in the endoscope 680 of FIG. 19.

Figure 20:
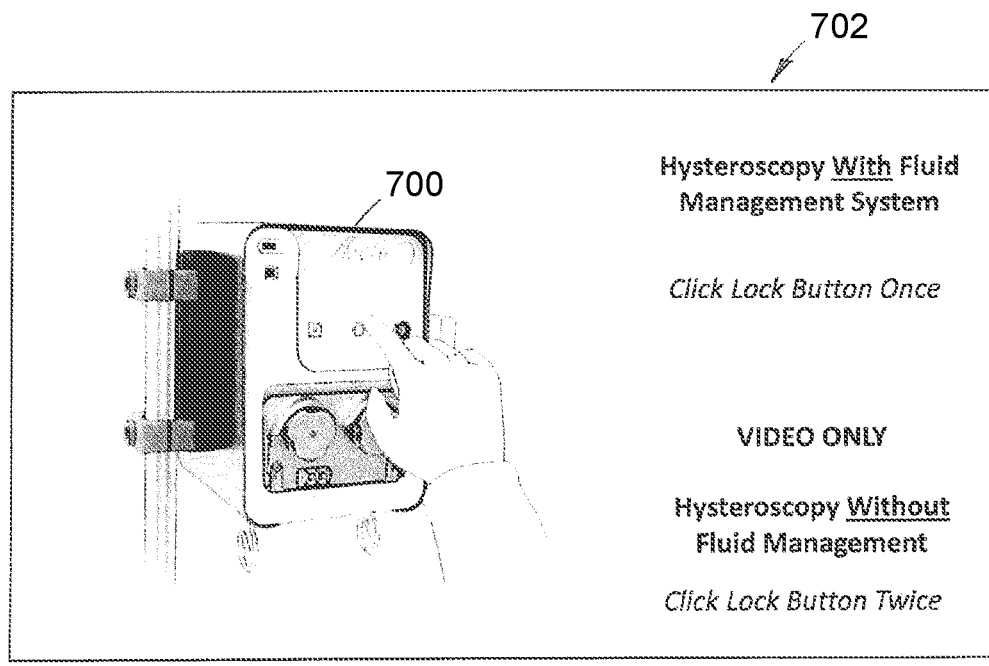
FIG. 20 illustrates another aspect of the control system of the endoscopic viewing system wherein the physician can (1) elect to operate the endoscope together with the fluid management system or (2) select use of the video only aspect of the endoscope without using the fluid management system.

Now turning to FIG. 20, another aspect of the fluid management system 700 as shown in FIGS. 1 and 10 is illustrated. It should be appreciated that in most hysteroscopic procedures for either diagnostics or therapeutics, the procedure time may be several minutes or more, and the physician will want to the fluid management system to provide fluid flows to distend the body cavity and to control the set pressure in the uterine cavity. The control actuators on the endoscope handle as described above are configured to control the fluid management system.

However, still referring to FIG. 20, in some cases the physician may be interested in only a quick diagnostic procedure and not want to use the fluid management system, which would entail connecting the cassette to the controller, etc. The physician may want a very simplified set up, for example connecting a saline bag with gravity feed to endoscope.

Thus, in order to provide all possible options to the physician, the control system corresponding to the invention includes an initial option when setting up the endoscopic system for use where the physician can select (1) use of the fluid management system or "video only" without use of the fluid management system. As is typical, the control system will provide screens 702 (FIG. 20) to prompt the physician or nurse to follow all the setup steps. FIG. 20 shows an initial step in which the physician or nurse can elect to use the fluid management system or to use "video only". In FIG. 20, the screen indicates the option of pressing the lock button once or twice on the controller 700 to select use of the fluid management system or video only.

Figure 21:
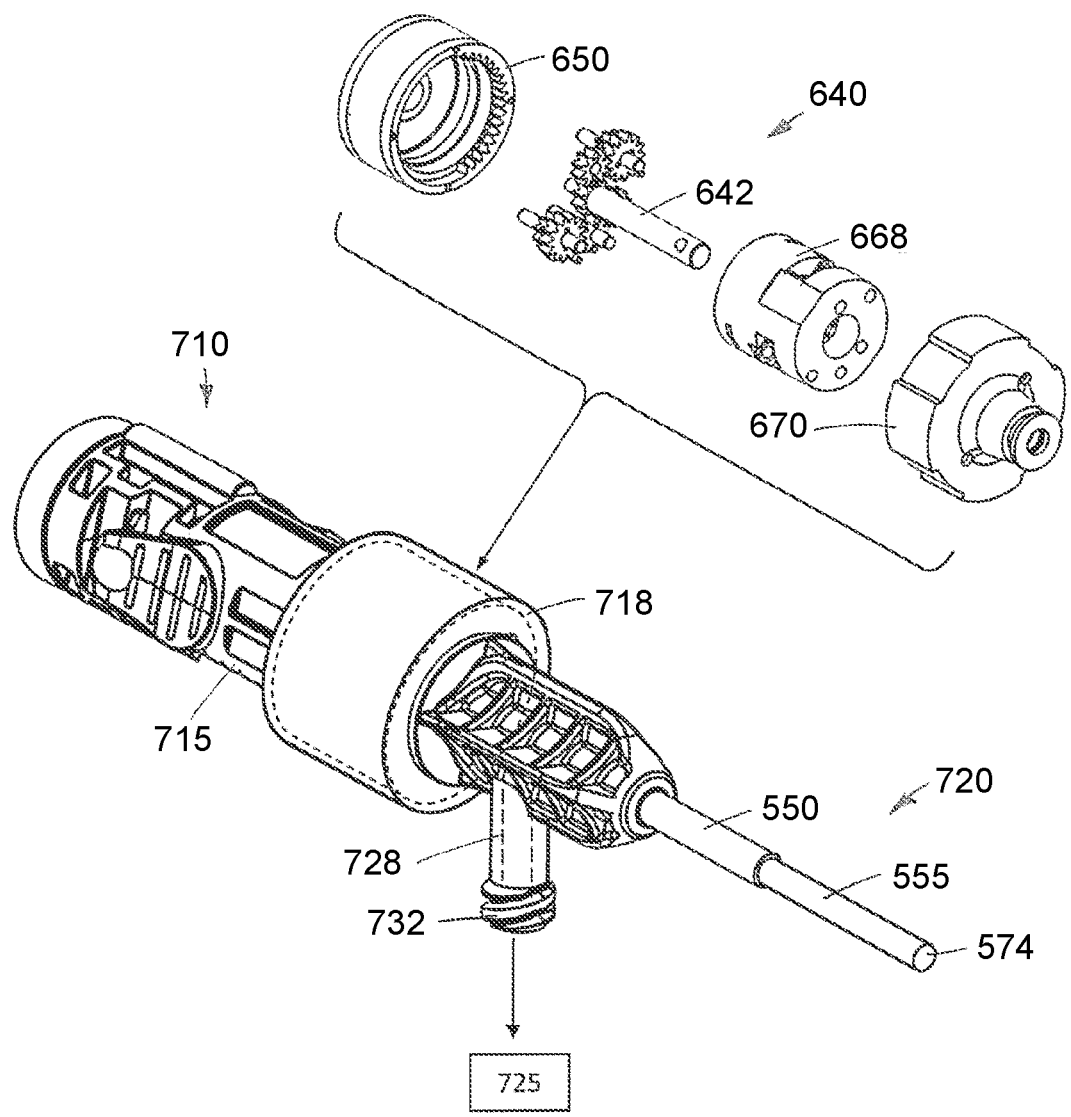
FIG. 21 is a perspective view of a proximal hub of a single-use tubular cutting assembly or resection component as depicted in FIG. 15, wherein the gear assembly of FIGS. 16-18A for converting the unidirectional rotation of the motor shaft into an oscillating rotational movement of the tubular cutting member is carried in the hub of the resection component.
Figure 22:
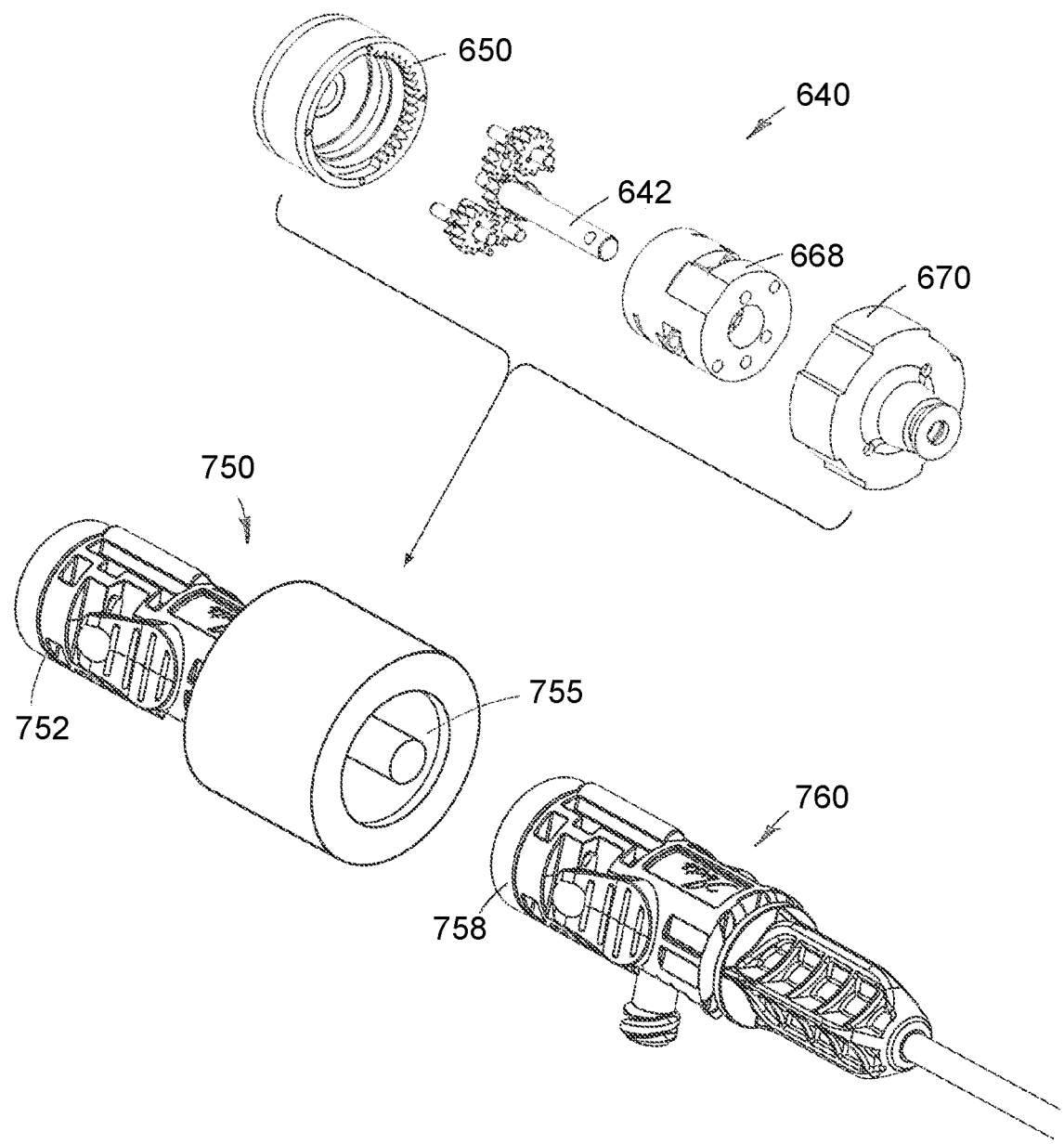
FIG. 22 is a perspective view of an independent adaptor component that carries the gear assembly of FIGS. 16-18A and is configured for coupling to motor-driven handpiece and further configured to receive a single-use tubular cutting assembly or resection device.

FIG. 21 illustrates another variation of the invention wherein a single-use tubular resecting probe 710 has a proximal hub 715 that detachably couples to a handpiece with a motor drive such as that of FIG. 15. In this variation, the hub 715 includes a housing that 718 that carries the gear assembly 640 of FIGS. 16-18A, which converts the unidirectional rotation of a motor shaft into an oscillating rotational movement of the tubular cutting member. FIG. 21 include an exploded view of components in the interior of housing 718, which includes outer ring gear 650, oscillating output shaft 642, pinion gear housing 668 and distal housing cap 670. The elongated shaft assembly 720 of the probe extends to a working end 548 as shown in FIG. 13, which includes outer sleeve 550 and rotating/oscillating inner sleeve 555 wherein the aspiration lumen 574 of FIG. 13 extends into the hub 715 (FIG. 21) and connects to an aspiration source 725 through channel 728 and connector 732. It can be seen that the aspiration lumen 574 extends to channel 728 and connector 732 that are disposed on the hub 715 distal to the housing 718 and gear mechanism 640. FIG. 22 illustrates another variation of the invention, which comprises an independent adaptor 750 that has a proximal end 752 that is configured for detachable coupling to a motor-drive handpiece and a distal end 755, which is configured to receive the hub 758 of a resecting device 760. It can be seen that housing portion 765 of the adaptor 750 carries the gear assembly 640 of FIGS. 16-18A and 21, which converts the unidirectional rotation of a motor shaft into an oscillating rotational movement of the tubular cutting member. The adapter can be a single-use component or can be re-useable.

In both the variation of FIGS. 21 and 22, the use such a single-use devices can be advantageous because various gear mechanisms 640 can be provided for selection by the user. For example, devices 710 and 750 can have different oscillations such as a single-rotation in each direction, two rotations in each direction, three rotations in each direction or four or more rotations in each direction. Further, the gear mechanism 640 can be adapted in separate devices 710 and 750 to have different rotational speeds ranging from 1,000 RPM to 15,000 RPM.

Although particular embodiments of the present invention have been described above in detail, it will be understood that this description is merely for purposes of illustration and the above description of the invention is not exhaustive. Specific features of the invention are shown in some drawings and not in others, and this is for convenience only and any feature may be combined with another in accordance with the invention. A number of variations and alternatives will be apparent to one having ordinary skills in the art. Such alternatives and variations are intended to be included within the scope of the claims. Particular features that are presented in dependent claims can be combined and fall within the scope of the invention. The invention also encompasses embodiments as if dependent claims were alternatively written in a multiple dependent claim format with reference to other independent claims.

Although particular embodiments of the present invention have been described above in detail, it will be understood that this description is merely for purposes of illustration and the above description of the invention is not exhaustive. Specific features of the invention are shown in some drawings and not in others, and this is for convenience only and any feature may be combined with another in accordance with the invention. A number of variations and alternatives will be apparent to one having ordinary skills in the art. Such alternatives and variations are intended to be included within the scope of the claims. Particular features that are presented in dependent claims can be combined and fall within the scope of the invention. The invention also encompasses embodiments as if dependent claims were alternatively written in a multiple dependent claim format with reference to other independent claims.

Other variations are within the spirit of the present invention. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. A single-use tissue resecting device comprising:
    an elongate handle carrying a motor having a drive shaft configured to rotate about a longitudinal axis, the motor drive shaft configured to rotate a ring gear and alternatively engage a first set of pinion gears and a second set of pinion gears;
    wherein the ring gear comprises a plurality of inwardly projecting gear teeth that extend less than 180° around the ring gear;
    wherein each gear of the first and second sets of pinion gears rotates about an axis aligned parallel with said longitudinal axis;
    wherein each of the first and second sets of pinion gears are intermediate the ring gear and a central output gear of an output shaft aligned parallel with the longitudinal axis;
    wherein rotation of the ring gear in a single rotational direction causes the first set of pinion gears to rotate the output shaft in a first rotational direction and the second set of pinion gears to rotate the output shaft in a second rotational direction to provide rotational oscillation of the output shaft; and
    a cutting member coupled to the output shaft such that rotation of the motor drive shaft in the single rotational direction causes rotational oscillation of the cutting member.

2. The tissue resecting device of claim 1, wherein the plurality of inwardly projecting gear teeth includes one or more gear teeth extending less inwardly than a remainder of the gear teeth for smooth meshing of the plurality of inwardly projecting gear teeth with the first set of pinion gears and the second set of pinion gears during rotation of the ring gear.

3. The tissue resecting device of claim 1, wherein a gear mechanism comprises the first and second sets of pinion gears, the ring gear, and the output shaft, wherein the gear mechanism is configured to rotationally oscillate the output shaft and cutting member in a sequence of 1 to 8 revolutions in each of the first rotational direction and the second rotational direction.

4. The tissue resecting device of claim 3, wherein the motor and the gear mechanism are configured to rotate the output shaft and cutting member in a range of 100 RPM to 5,000 RPM in each of the first rotational direction and the second rotational direction.

5. The tissue resecting device of 26, wherein the cutting member comprises an inner sleeve having an inner window, the inner sleeve rotatably positioned within an outer sleeve having an outer window, and rotation oscillation of the cutting member comprises rotational oscillation of the inner sleeve within the outer sleeve.

6. The tissue resecting device of claim 5, further comprising an aspiration lumen extending through the inner sleeve.

7. The tissue resecting device of claim 6, wherein the aspiration lumen extends to a port that is located distally of the gear mechanism.

8. The tissue resecting device of claim 5, wherein in a window-open position the inner window aligns with the outer window and in a window-closed position, the inner window is not aligned with the outer window.

9. The tissue resecting device of claim 8, wherein the inner sleeve comprises an outflow opening located on an opposite circumferential side of the inner window such that the outflow opening permits a fluid path into the inner sleeve during non-alignment of the inner window and the outer window.

10. The tissue resecting device of claim 5, wherein the gear mechanism is carried in a housing that is coupled to the inner sleeve and the outer sleeve, and the housing comprises a detachable component of the handle.

11. The tissue resecting device of claim 3, wherein the gear mechanism is carried in a housing that comprises a detachable component of the handle.

12. The tissue resecting device of claim 1, wherein the motor is a DC motor.

13. A single-use tissue resecting device comprising:
an elongate handle carrying a motor with a drive shaft that rotates around a longitudinal axis;
a gear mechanism coupled to the motor including a partial ring gear adapted to rotate around said longitudinal, a central output gear carried by an output shaft aligned with said longitudinal axis, and at least one pinion gear intermediate the ring gear and the output gear;
wherein the partial ring gear comprises a plurality of inwardly projecting gear teeth that extend less than 180° around the ring gear;
wherein the at least one pinion gear rotates about an axis parallel to the longitudinal axis; and
a cutting member coupled to the output shaft;
wherein rotation of the ring gear in a first rotational direction causes a pinion gear to rotate in a second rotational direction, wherein the gear mechanism causes rotational oscillation of the output shaft and cutting member; and
wherein the at least one pinion gear provides a gear reduction.

14. The tissue resecting device of claim 13, wherein the at least one pinion gear comprises a first set of pinion gears and a second set of pinion gears.

15. A single-use tissue resecting device comprising:
an elongate handle carrying a motor with a drive shaft that rotates around a longitudinal axis;
a gear mechanism coupled to the motor;
a cutting member coupled to an output shaft such that rotation of the drive shaft in a single rotational direction causes rotational oscillation of the cutting member;
wherein the gear mechanism comprises a partial ring gear adapted to engage a pinion gear assembly intermediate the ring gear and an output gear of the output shaft aligned parallel with said longitudinal axis, wherein the partial ring gear comprises a plurality of inwardly projecting gear teeth that extend less than 180° around the ring gear;
wherein the ring gear, the pinion gear assembly and the output gear are positioned in a plane transverse to said longitudinal axis to provide a compact assembly; and
wherein rotation of the ring gear in the single rotational direction rotates the output shaft in alternating first and second rotational directions to provide rotational oscillation of the output shaft and cutting member.

* * * * *